United States Patent
Okumura et al.

(10) Patent No.: US 7,003,076 B2
(45) Date of Patent: Feb. 21, 2006

(54) RADIATION DETECTOR, RADIATION DETECTING SYSTEM AND X-RAY CT APPARATUS

(75) Inventors: Miwa Okumura, Kawasaki (JP); Machiko Ono, Nasu-gun (JP); Toshihiro Rifu, Nasu-gun (JP); Tomiya Sasaki, Nasu-gun (JP); Michito Nakayama, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 123 days.

(21) Appl. No.: 10/679,494

(22) Filed: Oct. 7, 2003

(65) Prior Publication Data

US 2004/0071258 A1    Apr. 15, 2004

Related U.S. Application Data

(62) Division of application No. 09/928,211, filed on Aug. 13, 2001, now Pat. No. 6,658,082.

(30) Foreign Application Priority Data

| Aug. 14, 2000 | (JP) | 2000-245873 |
| Dec. 8, 2000 | (JP) | 2000-375144 |
| Jun. 12, 2001 | (JP) | 2001-177308 |

(51) Int. Cl.
 *H05G 1/64* (2006.01)

(52) U.S. Cl. .................. 378/98.8; 378/19; 250/370.09
(58) Field of Classification Search ................ 378/4, 378/19, 98.8; 250/208.1, 339.02, 370.08, 250/370.09, 370.11; 348/294, 308
See application file for complete search history.

(56) References Cited

U.S. PATENT DOCUMENTS

| 4,965,726 A | 10/1990 | Heuscher et al. ............. 378/19 |
| 5,430,784 A | 7/1995 | Ribner et al. ................. 378/19 |
| 6,157,696 A | 12/2000 | Saito et al. ................... 378/19 |
| 6,215,843 B1 | 4/2001 | Saito et al. ................... 378/19 |
| 6,535,571 B1 | 3/2003 | Von Der Haar ............... 378/19 |

FOREIGN PATENT DOCUMENTS

JP    06169912 A    6/1994

*Primary Examiner*—Edward J. Glick
*Assistant Examiner*—Courtney Thomas
(74) *Attorney, Agent, or Firm*—Oblon, Spivak, McClelland, Maier & Neustadt, P.C.

(57) ABSTRACT

A radiation detector of this invention includes a scintillator for converting an X-ray incident from a surface side into light, at least one photodiode chip having a plurality of photodiodes for converting the converted light into electrical signals, at least one switching chip having a plurality of switching elements for reading out a plurality of signals from the plurality of photodiodes, and at least one data acquisition chip having a plurality of data acquisition systems for amplifying the plurality of readout signals and converting the signals into digital signals. The photodiode chip, the switching chip, and the data acquisition chip are commonly mounted on a rigid multilayer wiring board.

22 Claims, 20 Drawing Sheets

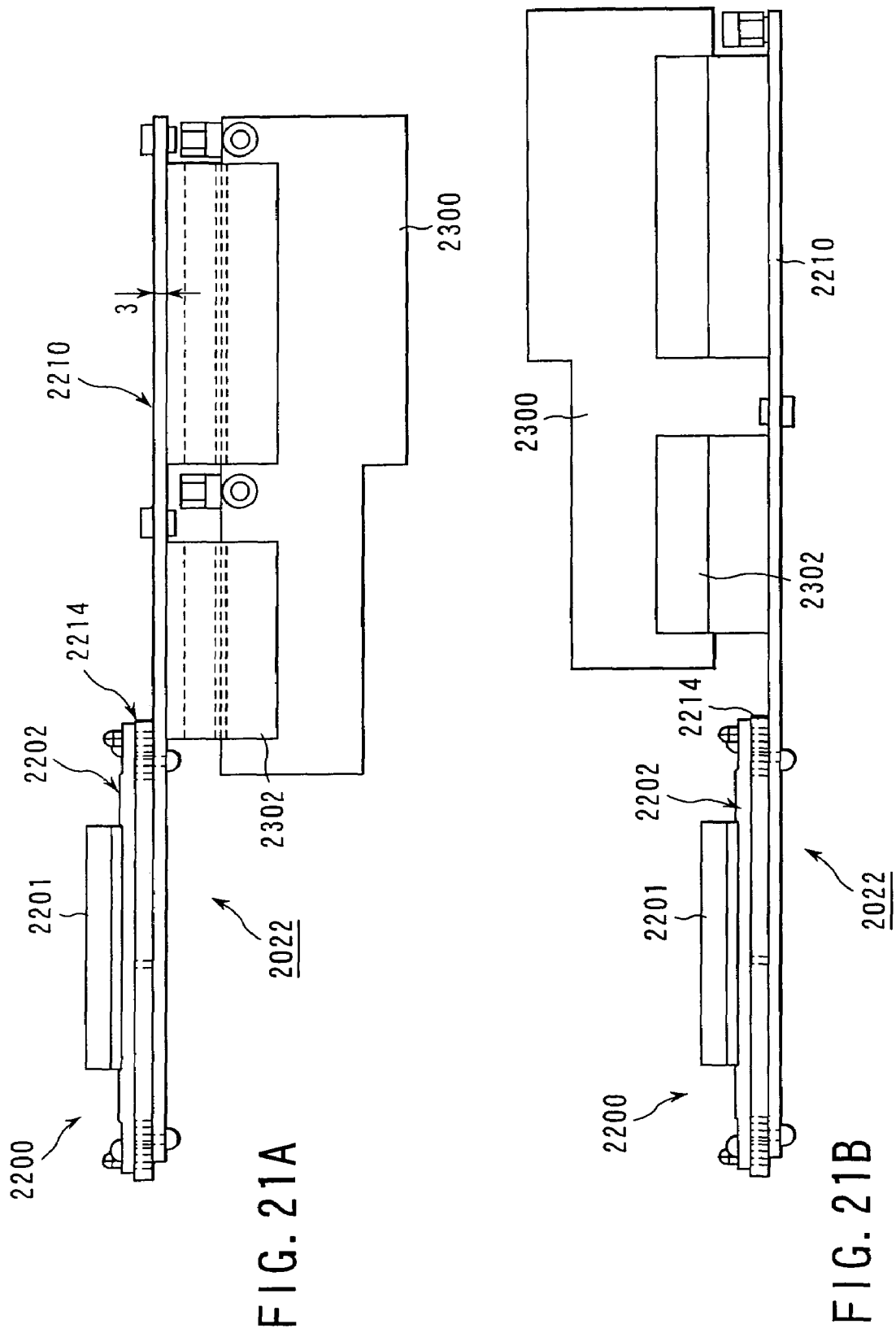

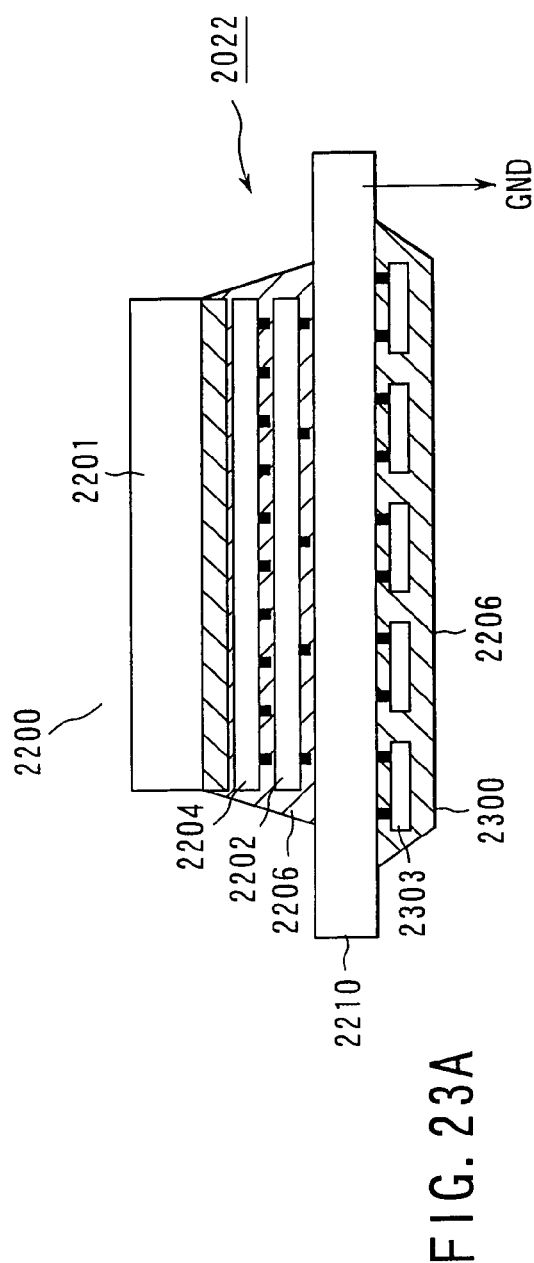
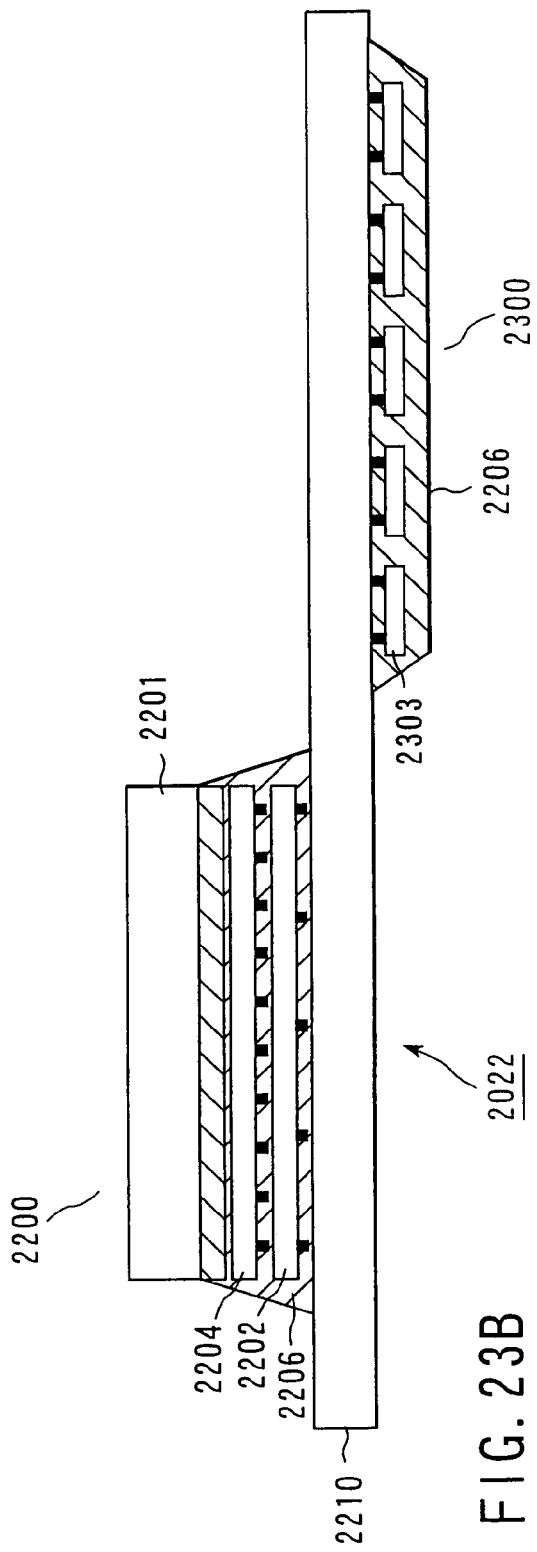
FIG. 23A
FIG. 23B

RADIATION DETECTOR, RADIATION DETECTING SYSTEM AND X-RAY CT APPARATUS

CROSS-REFERENCE TO RELATED APPLICATIONS

This application is a divisional of application Ser. No. 09/928,211, filed Aug. 13. 2001 now U.S. Pat. No. 6,658, 082, and claims the benefit of priority from the prior Japanese Patent Applications No. 2000-245873, filed Aug. 14, 2000; No. 2000-375144, filed Dec. 8, 2000; and No. 2001-177308, filed Jun. 12, 2001, each of which is incorporated herein by reference.

BACKGROUND OF THE INVENTION

1. Field of the Invention.

The present invention relates to a radiation detector or an X-ray computer tomography apparatus (to be referred to as an X-ray CT apparatus) having the radiation detector.

2. Description of the Related Art

An X-ray CT apparatus has an X-ray tube and radiation detector. The X-rays generated by the X-ray tube pass through an object to be examined and strike the radiation detector. The detector has a plurality of detection elements for detecting X-rays as an electrical signal. Each detection element includes a phosphor such as a scintillator for converting X-rays into light, and a photoelectric conversion element such as a photodiode for converting the light into charge (electrical signal). Recently, studies have been made to use a semiconductor element, as a detection element, which directly converts X-rays into charge.

A multislice type radiation detector has recently been introduced. The multislice type radiation detector has a plurality of detection element arrays arranged parallel along the slice direction. Each detection element array has a plurality of detection elements arranged in a line along the channel direction almost perpendicular to the slice direction.

This multislice type radiation detector is required to increase the number of detection element arrays. There was a limitation in the number of detection element arrays with the conventional radiation detector. The major factors that interfere with an increase in the number of radiation element arrays of the radiation detector are the inter-connection structure and connection structure. For the sake of descriptive convenience, assume that photodiodes are arranged in an n×m (channel direction×slide direction) matrix. That is, n photodiodes are arranged in the channel direction, and m photodiode arrays are arranged in the slice direction.

A plurality of photodiodes are connected to a plurality of switching elements through a plurality of signal extraction lines. The m signal extraction lines for the m photodiodes arranged in the slice direction are formed in the gap between this photodiode array and the adjacent photodiode array in the channel direction.

The number of photodiode arrays is therefore determined by the number of signal extraction lines that can be formed in the gap between the adjacent photodiode arrays in the channel direction. Although the number of signal extraction lines can be increased by increasing the gap, the area of the sensitivity range of each photodiode decreases in inverse proportion to the increase in gap, resulting in a deterioration in sensitivity.

BRIEF SUMMARY OF THE INVENTION

It is an object of the present invention to provide a radiation detector, radiation detecting system and X-ray CT apparatus which can increase the number of photodiode arrays.

A radiation detector according to the present invention comprises a scintillator for converting an X-ray incident from a surface side into light, at least one photodiode chip having a plurality of photodiodes for converting the converted light into electrical signals, at least one switching chip having a plurality of switching elements for reading out a plurality of signals from the plurality of photodiodes, and at least one data acquisition chip having a plurality of data acquisition systems for amplifying the plurality of readout signals and converting the signals into digital signals. The photodiode chip, the switching chip, and the data acquisition chip are commonly mounted on a rigid multilayer wiring board.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 21A is a sectional view of a detector module according to the eighth embodiment;

FIG. 21B is a sectional view of another detector module according to the eighth embodiment;

FIG. 23A is a sectional view of a detector module according to the eighth embodiment;

FIG. 23B is a sectional view of another detector module according to the eighth embodiment;

DETAILED DESCRIPTION OF THE INVENTION

The embodiments of the present invention will be described below with reference to the views of the accompanying drawing. The embodiments relate to a 2D array type radiation detector and an X-ray CT apparatus (X-ray computed tomography apparatus) equipped with the radiation detector. X-ray CT apparatuses are classified into various types, e.g., a rotate/rotate type in which an X-ray tube and radiation detector rotate together around an object to be examined, and a stationary/rotate type in which many detection elements arrayed in the form of a ring, and only an X-ray tube rotates around an object. The present invention can be applied to any of these types. In this case, the X-ray CT apparatus will be described as a rotate/rotate type, which has recently become the mainstream.

To reconstruct 1-volume (=one volume data) voxel data (or one tomographic image) (to be described later), projection data corresponding to one rotation around an object, i.e., about 360°, is required. In the half scan method, projection data corresponding to about 210 to 240° is required. The present invention can be applied to either scheme. Assume that the former general scheme is used, in which 1-volume voxel data (or one tomographic image) is reconstructed from projection data corresponding to about 360°.

The mainstream mechanisms for converting incident X-rays into charge are an indirect conversion type in which X-rays are converted into light by a phosphor such as a scintillator, and the light is converted into charge by photoelectric conversion elements such as photodiodes, and a direction conversion type using a photoconductive phenomenon in which electron-hole pairs are generated in a semiconductor by specific X-rays and move to electrodes. Although X-ray detection elements use either scheme, the present invention will be described hereinafter by taking the former indirect conversion type as an example.

In the following description, the width of sensitivity range of a photodiode is defined as a value converted on the rotation center axis of the X-ray tube. More specifically, a "photodiode having a sensitivity range width of 1 mm" is a photodiode having a sensitivity range width equivalent to 1 mm on the rotation center axis of the X-ray tube. In consideration of radial diffusion of X-rays, the actual sensitivity range width of a photodiode is slightly larger than 1 mm according to the ratio of the actual distance from the X-ray focal point and the sensitivity range of the photodiode to the actual distance from the X-ray focal point and the rotation center axis.

First Embodiment

Figure 1:
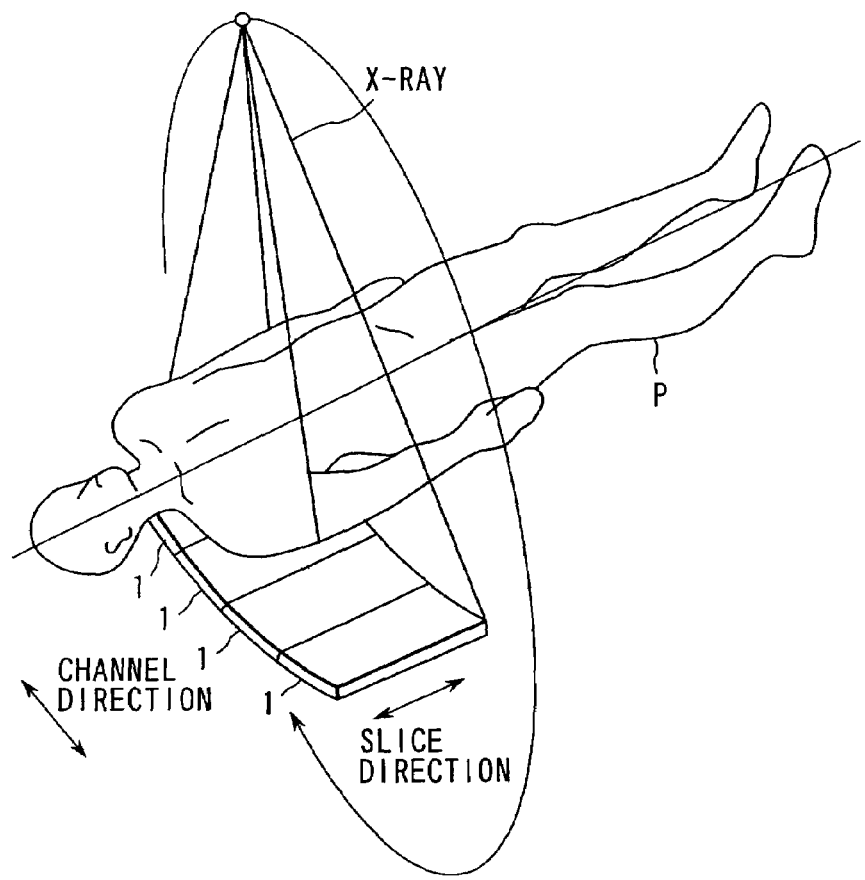
FIG. 1 is a perspective view of a radiation detector according to the first embodiment of the present invention.
Figure 2B:
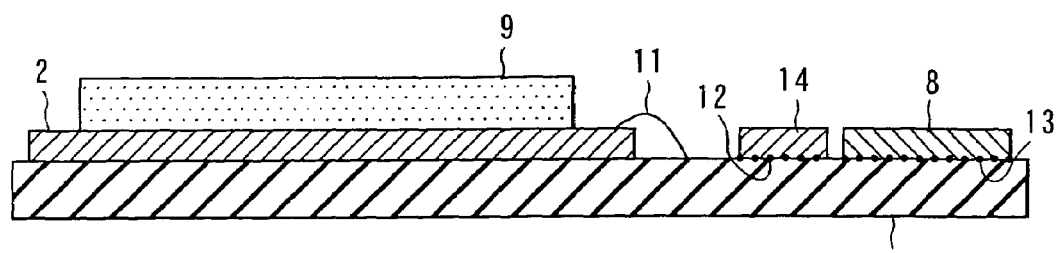
FIGS. 2A and 2B are views showing the arrangement of one photodiode array of the radiation detector according to the first embodiment of the present invention.
Figure 2A:
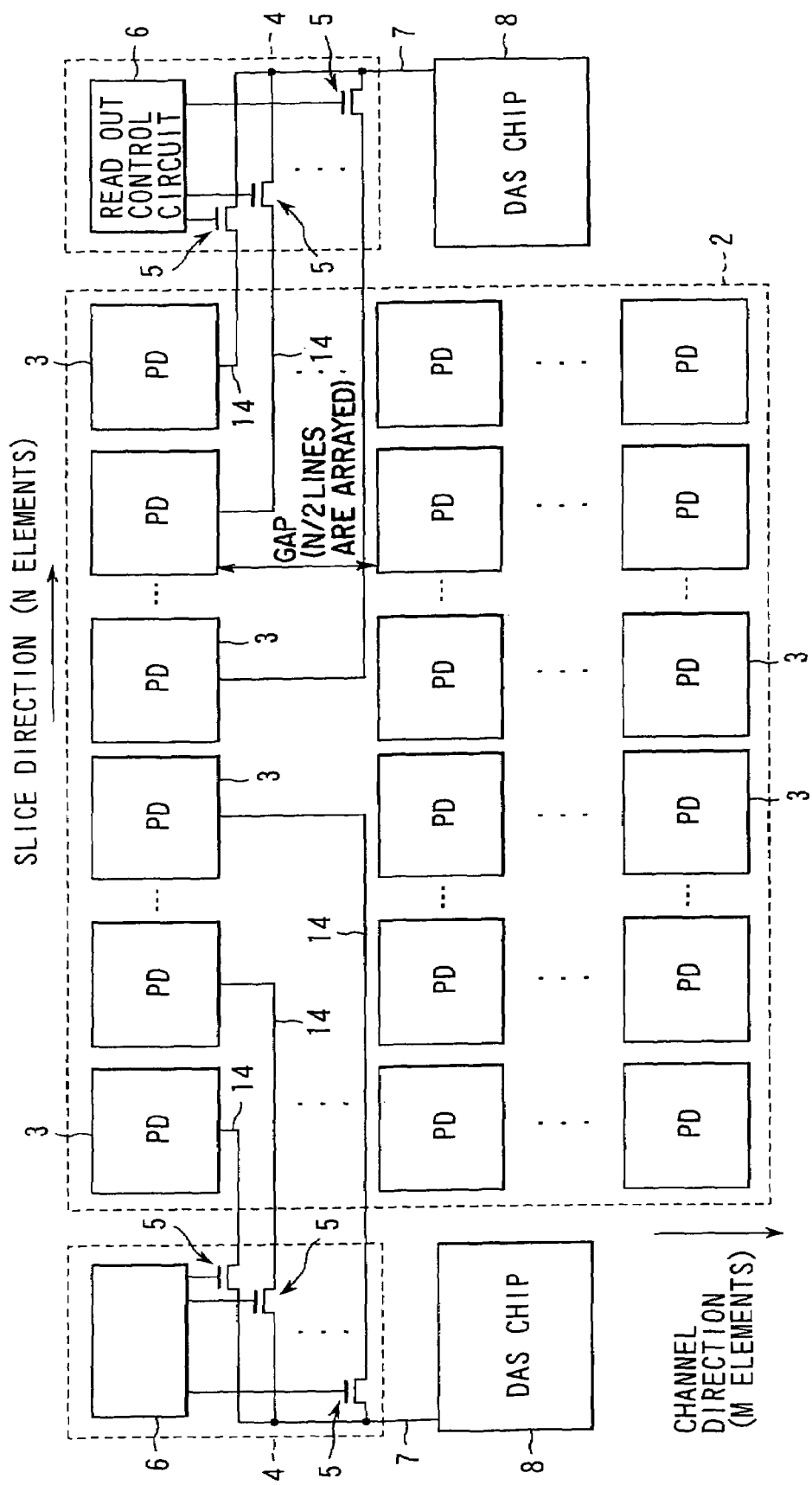

FIG. 1 is a perspective view of a radiation detector according to the first embodiment. The radiation detector is comprised of a plurality of detector modules 1 arranged in an almost arcuated form along the slice direction. FIG. 2A schematically shows the arrangement of one detector module 1. FIG. 2B shows a cross-sectional portion of one detector module 1.

Each detector module 1 is formed by commonly mounting, on one rigid ceramic printed wiring board 10, a scintillator 9 for converting incident radiation (X-rays in this case) into light, at least one photodiode chip 2 for converting the converted light into an electrical signal, at least one switching chip 4 for reading out the electrical signal from the photodiode chip 2, and at least one DAS (Data Acquisition System) chip 8 for amplifying the readout electrical signal and digitizing it. The rigid printed wiring board 10 is longer in the slice direction than in the channel direction. The photodiode chip 2, switching chip 4, and DAS chip 8 are arranged on the rigid printed wiring board 10 along the slice direction.

The photodiode chip 2 is obtained by forming a plurality of photodiodes 3 and a plurality of Al interconnections 14 on the surface of a silicon substrate. The N photodiodes 3 are spaced apart from each other by a predetermined gap in the slice direction. The M photodiodes 3 are spaced apart from each other by a predetermined gap in the channel direction.

Note that the slice direction is almost parallel to the body axis of the object, and the channel direction is almost perpendicular to the body axis of the object.

The plurality of Al interconnections 14 are connected to the plurality of photodiodes 3, respectively. The (N/2)×M photodiodes 3 arranged in the right half area on the photodiode chip 2 in the slice direction are electrically extracted outside to the right through the (N/2)×M Al interconnections 14 formed in the gap in a direction almost parallel to the slice direction. The (N/2) Al interconnections 14 corresponding to the (N/2) photodiodes 3 in the same slice array are formed at a high density in the gap between this slice array and the adjacent slice array.

The (N/2)×M photodiodes 3 arranged in the left half area on the photodiode chip 2 in the slice direction are electrically extracted outside to the left through the (N/2)×M Al interconnections 14 formed in the gap in a direction almost parallel to the slice direction. The (N/2) Al interconnections 14 corresponding to the (N/2) photodiodes 3 in the same slice array are formed at a high density in the gap between this slice array and the adjacent slice array.

The Al interconnections 14 extracted to the left and right are commonly connected to signal readout lines 7, (N/2) lines at a time, through transistors 5.

The number of interconnections 14 to be formed in a gap is determined by the width of the gap, the thickness of each interconnection 14, and the spacing between the interconnections 14. The number of photodiodes 3 arrayed in the slice direction (slice element count) is determined by the number of interconnections. In this embodiment, since the interconnections 14 are separately extracted to the left and right, the number of photodiodes 3 arrayed in the slice direction is twice the number of interconnections 14 that can be formed in a gap.

Each switching chip 4 is obtained by forming a plurality of CMOS transistors 5 as switching elements on a silicon substrate. The plurality of transistors 5 are respectively connected to the plurality of photodiodes 3. The N/2 photodiodes 3 arranged on the same slice array on the same side are commonly connected to the signal readout line 7 through the N/2 interconnections 14 and N/2 transistors 5. The DAS chip 8 is connected to the signal readout line 7.

When the transistor 5 is turned on, the charge stored in the photodiode 3 is read out as a current signal to the signal readout line 7. The ON/OFF operation (gate voltage) of the transistor 5 is controlled by a readout control circuit 6. As described above, since the N/2 interconnections 14 arranged in the slice direction are commonly connected to the signal readout line 7, signals in the N/2 photodiodes 3 can be sequentially read out by sequentially turning on the corresponding N/2 transistors 5. In addition, since the DAS chip 8 is connected to each signal readout line 7, signals can be completely read out from all the photodiodes 3 in the module in the time required to serially read out signals from the N/2 photodiodes 3.

When a plurality of transistors 5 corresponding to adjacent photodiodes 3 are turned on at once, signals from the photodiodes 3 can be added in an analog manner. In this case, the plurality of photodiodes 3 constitute one channel. The slice thickness can be arbitrarily changed by such interconnection structure and electronic readout control.

The plurality of Al interconnections 14 connected to the plurality of photodiodes 3 are connected to a plurality of contact points on the rigid printed wiring board 10 through a plurality of metal wires 11 by a wire bonding technique. A plurality of bumps 12 formed on the surface of the switching chip 4 are soldered to a plurality of corresponding bumps formed on the surface of the rigid printed wiring board 10. At the same time, a plurality of bumps 13 formed on the surface of the DAS chip 8 are soldered to a plurality of corresponding bumps formed on the surface of the printed wiring board 10 by a flip chip technique.

As described above, since the Al interconnections 14 are extracted to the left and right, the number of photodiodes 3 that can be formed in the slice direction can be doubled as compared with a case where the Al interconnections 14 are extracted in only one direction. In addition, the wire bonding area between the rigid printed wiring board 10 and the photodiode chip 2 can be increased by extracting the Al interconnections 14 to the left and right. This arrangement can therefore cope with an increase in the number of photodiodes 3.

By mounting the photodiode chip 2, switching chip 4, and DAS chip 8 on the one rigid printed wiring board 10, these three components can be easily connected to each other. This technique can therefore cope with an increase in the number of photodiodes 3.

By commonly connecting the Al interconnections 14 to the signal readout line 7, the number of signal readout lines between the switching chip 4 and the DAS chip 8 can be reduced. In addition, the simple arrangement in which the N/2 interconnections 14 are commonly connected to the signal readout line 7 allows the slice thickness to be easily changed by electronic control on the transistors 5.

Second Embodiment

In the first embodiment, a plurality of photodiodes are electrically extracted by using a plurality of Al interconnections formed on the surface of a silicon substrate. For this reason, the number of Al interconnections, i.e., the number of photodiodes arrayed (element count) in the slice direction, is limited by the width of the gap between photodiodes in which Al interconnections are formed.

In the second embodiment, the above limitation is reduced by electrically extracting a plurality of photodiodes to the lower surface of a silicon substrate through via interconnections extending through the silicon substrate from the upper surface to the lower surface.

Figure 3:
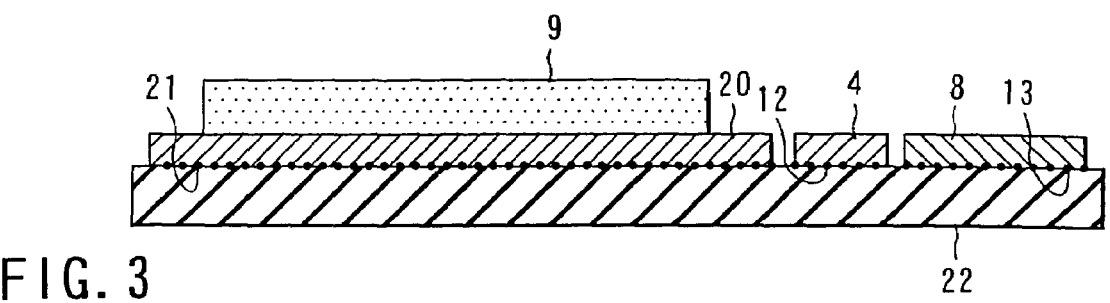
FIG. 3 is a sectional view of a radiation detector according to the second embodiment.
Figure 4:
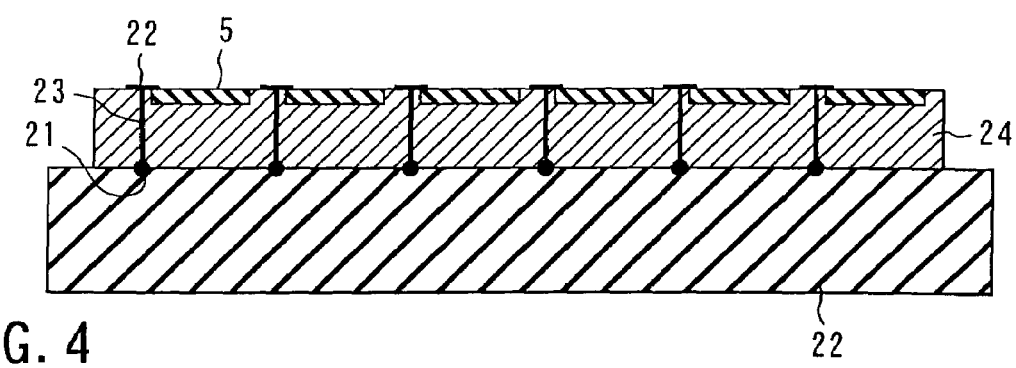
FIG. 4 is a sectional view showing connection between a photodiode chip and a rigid printed wiring board in FIG. 3.

FIG. 3 is a sectional view of a detector module forming a radiation detector according to the second embodiment. FIG. 4 is a sectional view showing the via interconnection structure in FIG. 3 in detail. At least one photodiode chip 20, at least one switching chip 4, and at least one DAS chip 8 are commonly mounted on a rigid ceramic printed wiring board 22.

A plurality of bumps 12 formed on the surface of the switching chip 4 are soldered to a plurality of bumps formed on the surface of the rigid printed wiring board 22 by a flip chip technique. Likewise, a plurality of bumps 13 formed on the surface of the DAS chip 8 are soldered to a plurality of bumps formed on the surface of the rigid printed wiring board 22 by the flip chip technique.

A plurality of photodiodes 5 are formed on the surface of a silicon substrate 24 in the form of a matrix. The plurality of photodiodes 5 are respectively connected to a plurality of Al interconnections 22 formed on the surface of the silicon substrate 24. The plurality of Al interconnections 22 are respectively connected to a plurality of via interconnections 23 extending through the silicon substrate 24 from the upper surface to the lower surface. The side surfaces of the plurality of via interconnections 23 are insulated by, for example, silicon oxide. A plurality of bumps 21 are formed on the lower surface of the silicon substrate 24 at the rear ends of the plurality of via interconnections 23. As described above, the plurality of photodiodes 5 are electrically extracted to the lower surface through the plurality of via interconnections 23.

The plurality of bumps 21 formed on the lower surface of the silicon substrate 24 are soldered to a plurality of corresponding bumps formed on the upper surface of the rigid printed wiring board 22.

Since the plurality of photodiodes 5 are electrically extracted to the lower surface of the substrate through the plurality of via interconnections 23 in this manner, the above limitation on the number of photodiodes 5 arrayed (element count) in the slice direction can be eliminated to increase the number of photodiodes 5.

Third Embodiment

A radiation detector is housed in the gantry housing of an X-ray CT apparatus. The width of a detector module in the slice direction is limited by the size of the internal space of the gantry housing. As described above, when a photodiode chip, switching chip, and DAS chip are to be commonly mounted on a rigid printed wiring board, the mount area of the photodiode chip is restricted by the switching chip and DAS chip. Therefore, the number of photodiodes 5 (element count) arrayed in the slice direction is limited by the mount area of the photodiode chip.

According to the third embodiment, this limitation is reduced.

Figure 5:
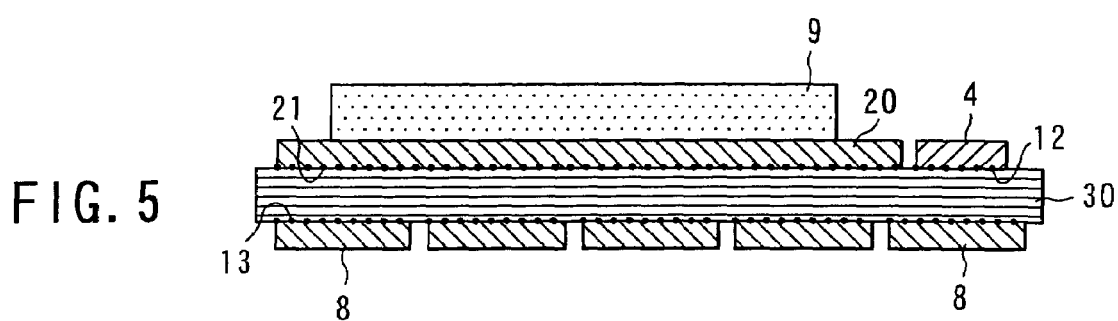
FIG. 5 is a sectional view of a radiation detector according to the third embodiment.

FIG. 5 is a sectional view of a detector module forming a radiation detector according to the third embodiment. At least one photodiode chip 20 and at least one switching chip 4 are mounted on the upper surface of a rigid multilayer wiring board 30. At least one DAS chip 8 is mounted on the lower surface of the rigid multilayer wiring board 30. By mounting the DAS chip 8 on the lower surface, the width of the detector module in the slice direction can be increased to increase the number of photodiodes 5 (element count) arrayed in the slice direction.

A plurality of photodiodes of the photodiode chip 20 are connected to a plurality of terminals of printed interconnections formed on the upper surface of the multilayer wiring board 30 through a plurality of via interconnections extending through the silicon substrate from the upper surface to the lower surface, and further connected to a plurality of transistors of the switching chip 4 through surface printed interconnections.

A plurality of bumps 12 formed on the upper surface of the switching chip 4 are connected to a plurality of bumps formed on the upper surface of the rigid multilayer wiring board 30 with solder 35 by the flip chip technique.

A plurality of bumps 13 formed on the upper surface of the DAS chip 8 are soldered to a plurality of corresponding bumps formed on the lower surface of the rigid multilayer wiring board 30 by the flip chip technique.

Figure 6:
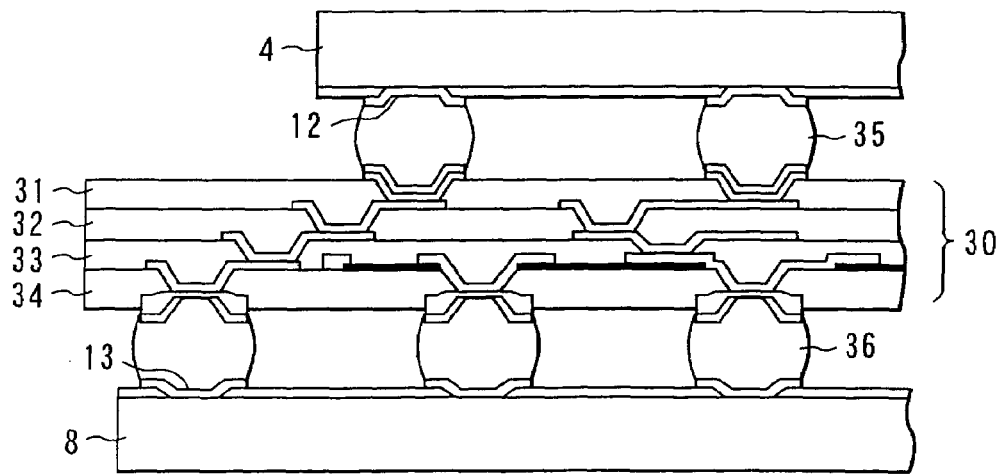
FIG. 6 is a sectional view of a multilayer wiring board in FIG. 5.

FIG. 6 shows the sectional structure of the multilayer wiring board 30. The multilayer wiring board 30 is comprised of a plurality of thin wiring boards 31 to 34 stacked on each other. The plurality of wiring boards 31 to 34 are connected to each other through a plurality of via holes.

Routing of the respective wiring boards 31 to 34 and connection of interconnections between the wiring boards 31 to 34 are so designed as to connect the plurality of bumps 12 of the switching chip 4 to the corresponding bumps 13 of the DAS chip 8.

As described above, the DAS chip 8 can be mounted on the lower surface by using the multilayer wiring board 30. This makes it possible to increase the amount area of the photodiode chip, limited by the DAS chip 8, and increase the number of photodiodes 5 (element count) arrayed in the slice direction.

Fourth Embodiment

Figure 7:
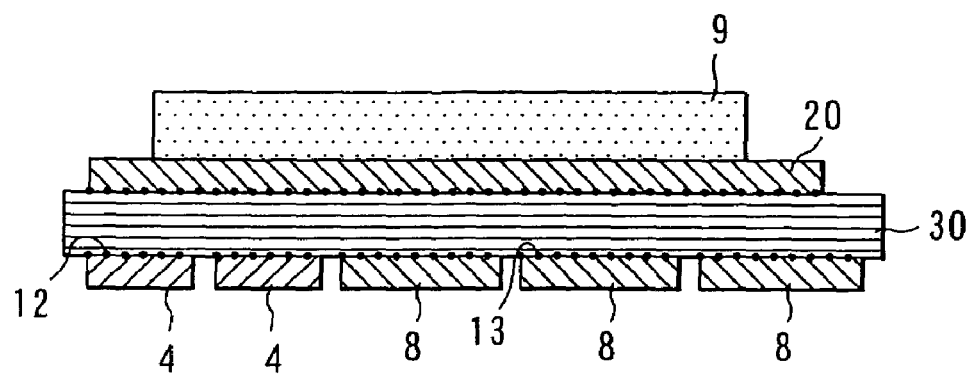
FIG. 7 is a sectional view of a radiation detector according to the fourth embodiment.

FIG. 7 is a sectional view of a detector module according to the fourth embodiment.

In the third embodiment, the photodiode chip and switching chip are mounted on the upper surface of the multilayer wiring board, and the DAS chip is mounted on the lower surface of the multilayer wiring board to increase the mount area of the photodiode chip.

In contrast to this, in the fourth embodiment, only a photodiode chip 20 is mounted on the upper surface of a multilayer wiring board 40, and both a DAS chip 8 and a switching chip 4 are mounted on the lower surface of the multilayer wiring board 40 to further increase the mount area of the photodiode chip 20.

A plurality of photodiodes of the photodiode chip 20 are connected to a plurality of terminals formed on the upper surface of the multilayer wiring board 40 through a plurality of via interconnections extending through the silicon substrate from the upper surface to the lower surface.

A plurality of bumps 12 formed on the upper surface of the switching chip 4 are soldered to a plurality of corresponding bumps formed on the lower surface of the multilayer wiring board 40 by the flip chip technique.

A plurality of bumps 13 formed on the upper surface of the DAS chip 8 are soldered to a plurality of corresponding bumps formed on the lower surface of the multilayer wiring board 40 by the flip chip technique.

Routing of interconnections of a plurality of wiring boards constituting the multilayer wiring board 40 and connection of interconnections between the plurality of wiring boards are so designed as to connect the plurality of photodiodes of the photodiode chip 20 to the plurality of corresponding transistors of the switching chip 4.

As described above, by mounting only the photodiode chip 20 on the upper surface of the multilayer wiring board 40 and mounting both the switching chip 4 and the DAS chip 8 on the lower surface of the multilayer wiring board 40, the mount area of the photodiode chip 20 can be further increased to increase the number of photodiodes 5 (element count) arrayed in the slice direction.

Fifth Embodiment

Figure 8:
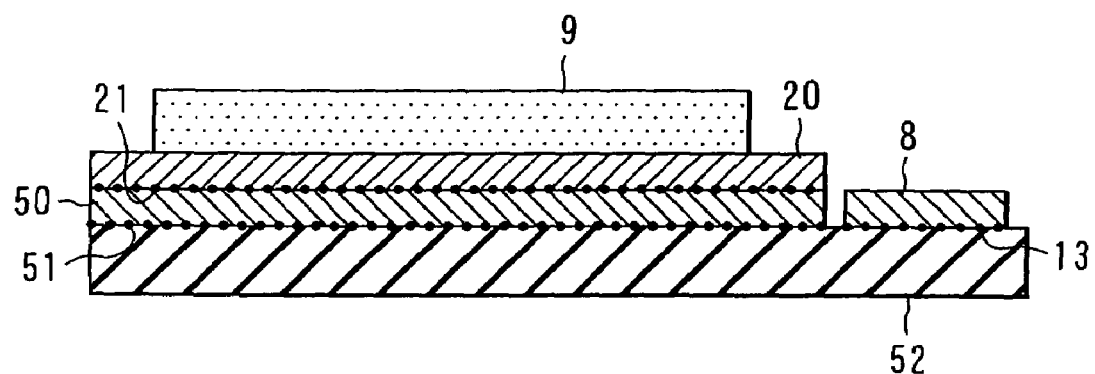
FIG. 8 is a sectional view of a radiation detector according to the fifth embodiment.

FIG. 8 is a sectional view of a detector module forming a radiation detector according to the fifth embodiment. A switching chip 50 and DAS chip 8 are mounted on a rigid ceramic printed wiring board 52, and a photodiode chip 20 is mounted on the upper surface of the switching chip 50.

A plurality of bumps are formed on the upper surface of the switching chip 50 and soldered to a plurality of bumps on the lower surface of the photodiode chip 20. A plurality of bumps 51 are formed on the lower surface of the switching chip 50 and connected to a plurality of transistors on the upper surface through via interconnections. The plurality of bumps 51 on the lower surface of the switching chip 50 are soldered to a plurality of corresponding bumps formed on the upper surface of the rigid printed wiring board 52. Likewise, a plurality of bumps 13 formed on the upper surface of the DAS chip 8 are soldered to the plurality of bumps formed on the upper surface of the rigid printed wiring board 52 by the flip chip technique.

Even if the photodiode chip 20 is mounted on the upper surface of the switching chip 50 in this manner, the same effect as that of the third embodiment can be obtained.

Sixth Embodiment

Figure 9:
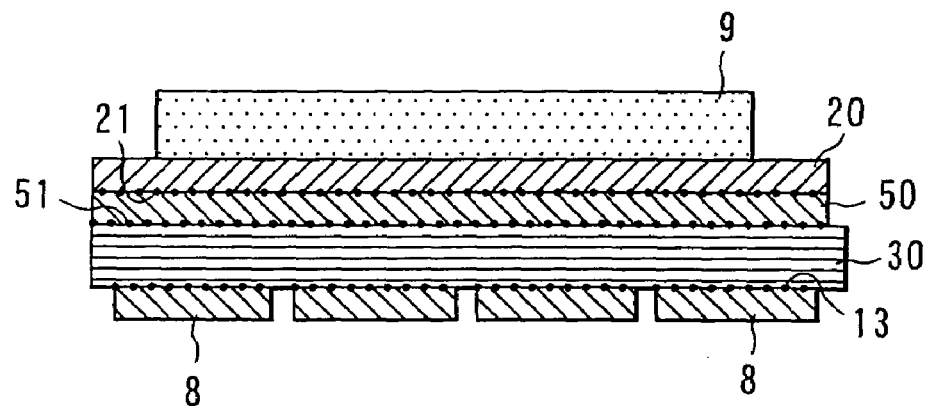
FIG. 9 is a sectional view of a radiation detector according to the sixth embodiment.

FIG. 9 is a sectional view of a detector module forming a radiation detector according to the sixth embodiment. A switching chip 50 is mounted on the upper surface of a rigid multilayer wiring board 60, and a DAS chip 8 is mounted on the lower surface of the rigid multilayer wiring board 60. A photodiode chip 20 is mounted on the upper surface of the switching chip 50.

A plurality of bumps are formed on the upper surface of the switching chip 50 and soldered to a plurality of bumps on the lower surface of the photodiode chip 20. A plurality of bumps 51 are also formed on the lower surface of the switching chip 50 and connected to a plurality of transistors on the upper surface through via interconnections. The plurality of bumps 51 on the lower surface of the switching chip 50 are soldered to a plurality of corresponding bumps formed on the upper surface of the multilayer wiring board 60. A plurality of bumps 13 formed on the upper surface of the DAS chip 8 are soldered to a plurality of bumps formed on the lower surface of the multilayer wiring board 60 by the flip chip technique.

Routing of interconnections of a plurality of wiring boards constituting the multilayer wiring board 60 and connection of the interconnections between the plurality of wiring boards are so designed as to connect a plurality of transistors on a switching chip 4 to a plurality of corresponding bumps on the DAS chip 8.

Even if the photodiode chip 20 is mounted on the upper surface of the switching chip 50 and the DAS chip 8 is mounted on the lower surface of the multilayer wiring board 60 in this manner, the same effect as in the fourth embodiment can be obtained.

As described above, the first to sixth embodiments are applied in various forms as described above, and can implement practical, significant arrangements.

Seventh Embodiment

Figure 10:
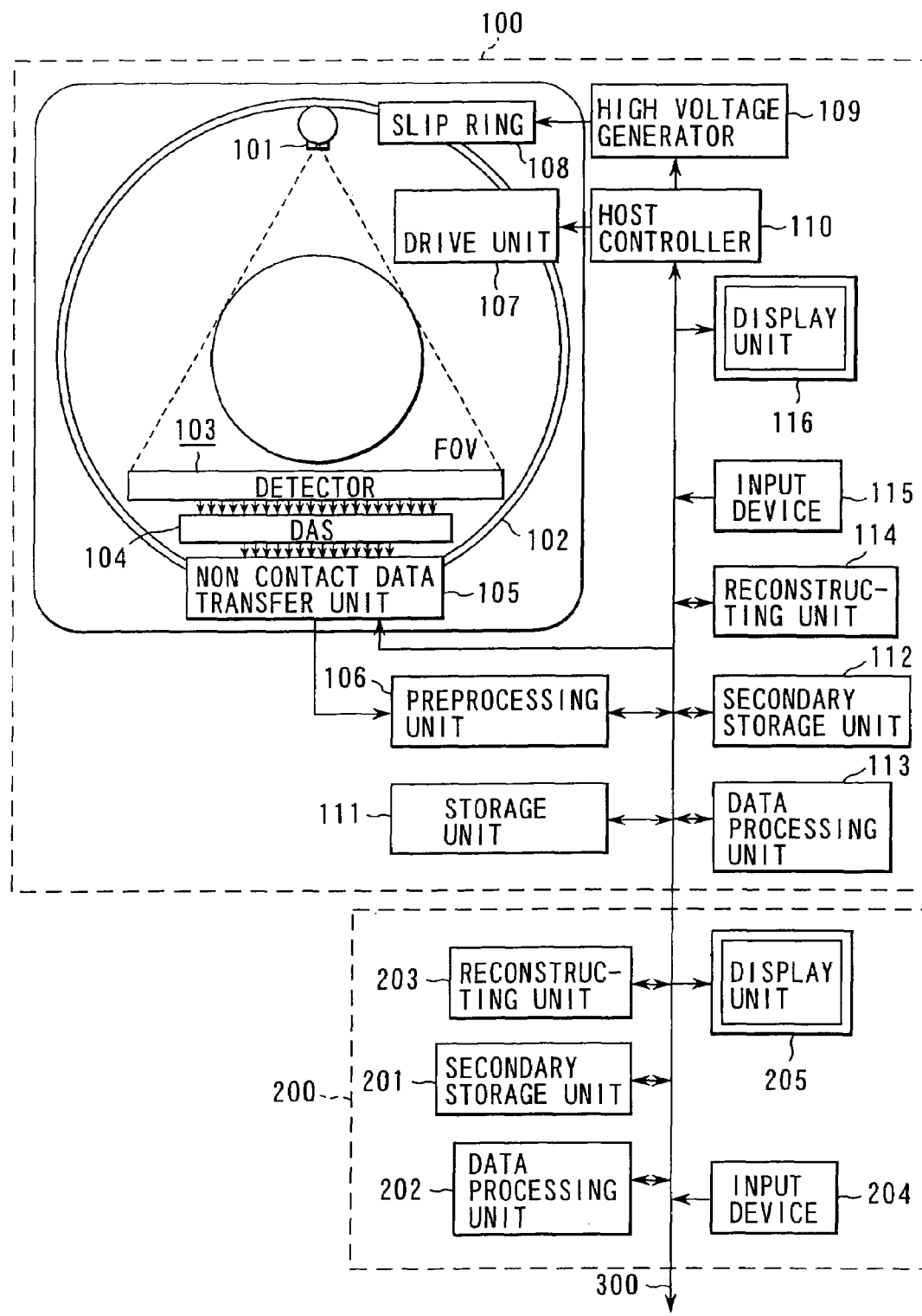
FIG. 10 is a view showing the arrangement of an X-ray CT apparatus according to the seventh embodiment.

FIG. 10 shows the arrangement of an X-ray CT apparatus according to the seventh embodiment. A rotating ring 102 is driven by a gantry drive unit 107 at a speed as high as one second or less per rotation. An X-ray tube 101 for emitting an X-ray cone beam (quadrature pyramid) or fan beam onto an object P placed in an effective field of view FOV is mounted on the rotating ring 102. Power required for the radiation of X-rays is supplied from a high voltage generator 109 to the X-ray tube 101 through a slip ring 108. With this operation, the X-ray tube 101 generates a so-called X-ray cone beam or fan beam that diverges in two directions, i.e., a channel direction C perpendicular to the body axis direction of the object and a slice direction A (=a direction parallel to the rotation axis) perpendicular to the channel direction C.

Figure 11:
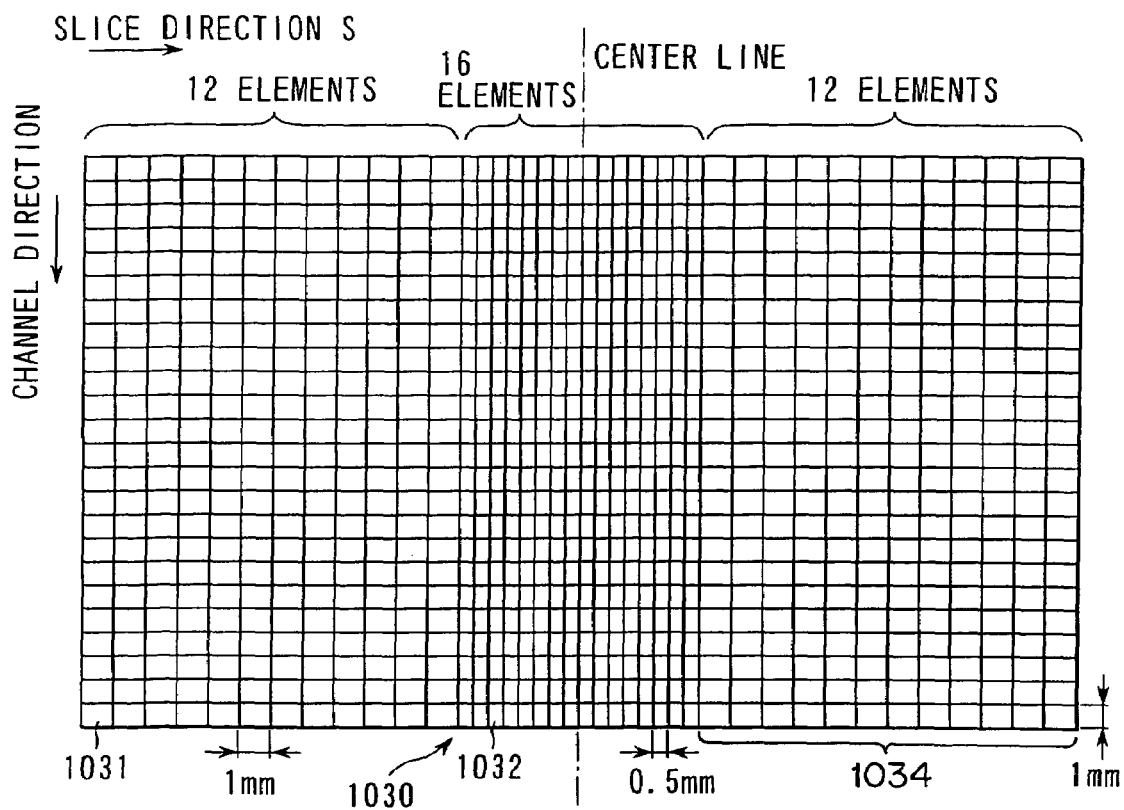
FIG. 11 is a plan view of one detector module in FIG. 10.

A radiation detector 103 for detecting X-rays passing through the object P is mounted on the rotating ring 102 in a position to oppose the X-ray tube 101. The radiation detector 103 is constituted by a plurality of (e.g., 38) detector modules. FIG. 11 is a developed view of one detector module. A detector module 1030 includes a scintillator and a photodiode chip having a plurality of detection elements comprising photodiodes 1031 and 1032. The plurality of detection elements 1031 and 1032 are arranged in the form of a matrix in two directions, i.e., the channel direction C and the slice direction S. The plurality of detector modules 1030 of the X-ray CT apparatus of this embodiment are not arranged two-dimensionally but are arranged along an arc centered on the focal point of the X-ray tube 101.

As described above, the detector module 1030 includes a switching chip and DAS chip as well as the photodiode chip having the plurality of detection elements 1031 and 1032, as described above. These photodiode chip, switching chip, and DAS chip are mounted on a single rigid printed wiring board.

One detection element 1032 has a sensitivity range having a width of 0.5 mm in the slice direction and a width of 1 mm in the channel direction. The other detection element 1031 has a sensitivity range having a width of 1 mm in the slice direction and a width of 1 mm in the channel direction.

For example, 16 0.5-mm wide detection elements 1032 are arranged in the slice direction S. The 16 detection elements 1032 arranged in the slice direction S will be referred to as a first detection element array 1033. A plurality of 1-mm wide detection elements 1031 are arranged in the slice direction S in a number smaller than the number of detection elements 1032, e.g., 12, on each side of the first detection element array 1033. The 12 detection elements 1031 arranged in the slice direction S will be referred to as a second detection element array 1034.

In this embodiment, the number (e.g., 16) of detection elements 1032 arranged in the slice direction S is larger than the number (e.g., 12) of detection elements 1031 arranged on either side and smaller than the total number (e.g., 24) of detection elements 1031.

An enormous amount (data corresponding to M×N channels per view will be referred to as "2D projection data" hereinafter) of data about M×N (M=24 (elements)×38=912, and N=40 (=16 (elements)+2×12 (elements)) in this embodiment) detected by the radiation detector 103 are temporarily collected in a data acquisition system (DAS) 104 in the form of a chip, and are collectively transmitted to a data processing unit (to be described later) through a noncontact transfer unit 105 to which optical communication is applied.

The radiation detector 103 repeats detection about 1,000 times per rotation (about 1 sec). With this operation, an enormous amount of 2D projection data corresponding to M×N channels is generated 1,000 times per second (per rotation). To transmit such an enormous amount of 2D projection data, which is generated at high speed, without any delay, the data acquisition system 104 and noncontact transfer unit 105 are designed to perform ultra-high-speed processing.

In the data processing unit, a host controller 110 serving as a main component, a preprocessing unit 106 for performing preprocessing such as data correction, a storage unit 111, a secondary storage unit 112, a data processing unit 113, a reconstructing unit 114, an input device 115, and a display unit 116 are connected to each other through a data/control bus 300. In addition, an external image processing unit 200 constituted by a secondary storage unit 201, data processing unit 202, reconstructing unit 203, input unit 204, and display unit 205 is connected to the data processing unit through this bus 300.

The function/effect of the X-ray CT apparatus having the above arrangement will be described below. The following is a case (function) where volume data constituted by a plurality of voxel data is reconstructed on the basis of the object transmission X-ray data detected by the radiation detector 103, and various images such as a tomographic image of an arbitrary slice, a projection image from an arbitrary direction, and a 3D surface display image are reconstructed from the volume data.

Figure 12:
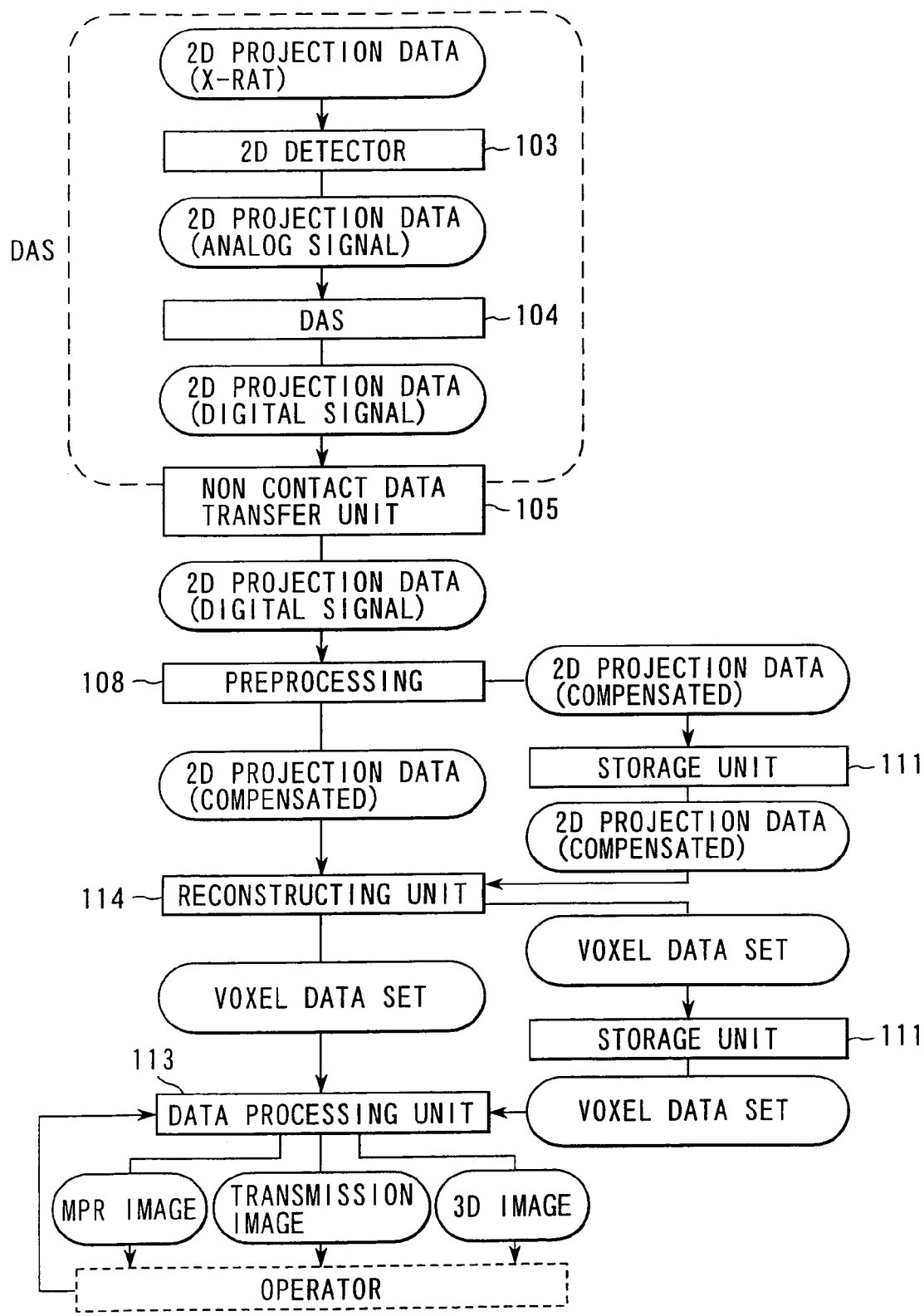
FIG. 12 is a flow chart showing the flow of data processing in the X-ray CT apparatus in FIG. 9.

FIG. 12 shows data processing and the flow of processing in the X-ray CT apparatus according to this embodiment. The X-rays passing through the object are converted into 2D projection data, which is an analog electrical signal, by the radiation detector 103. This data is converted into 2D projection data, which is a digital electrical signal, by the data acquisition system 104. The data is then sent to the preprocessing unit 106, which performs various types of correction, through the noncontact transfer unit 105 to be subjected to sensitivity correction and the like.

In the following description, the width of sensitivity range of a photodiode is defined as a value converted on the rotation center axis of the X-ray tube. More specifically, a "photodiode having a sensitivity range width of 1 mm" is a photodiode having a sensitivity range width equivalent to 1 mm on the rotation center axis of the X-ray tube. In consideration of radial diffusion of X-rays, the actual sensitivity range width of a photodiode is slightly larger than 1 mm according to the ratio of the actual distance from the X-ray focal point and the sensitivity range of the photodiode to the actual distance from the X-ray focal point and the rotation center axis.

In the radiation detector 103, the first detection element array group 1033 constituted by 0.5-mm wide detection elements 1032 converts X-ray detected near the central portion in a slice direction A into an analog electrical signal, whereas the second detection element array group 1034 constituted by 1-mm wide detection elements 1031, which are wider than the detection elements 1032, converts the remaining X-rays into an analog electrical signal. That is, the first detection element array group 1033 acquires 2D projection data and converts it into an analog electrical signal while keeping high resolution as compared with the remaining X-rays.

The X-ray tube 101 in the X-ray CT apparatus according to this embodiment generates an X-ray cone beam or fan beam, as described above. If a collimator having an appropriate arrangement is placed near this X-ray tube 101, the beam thickness of an X-ray cone beam or fan beam, i.e., the "slice width" (=the size of a bundle of a plurality of uniform "slice thicknesses" with respect to the object), can be changed by changing the aperture of the collimator.

Figure 13:
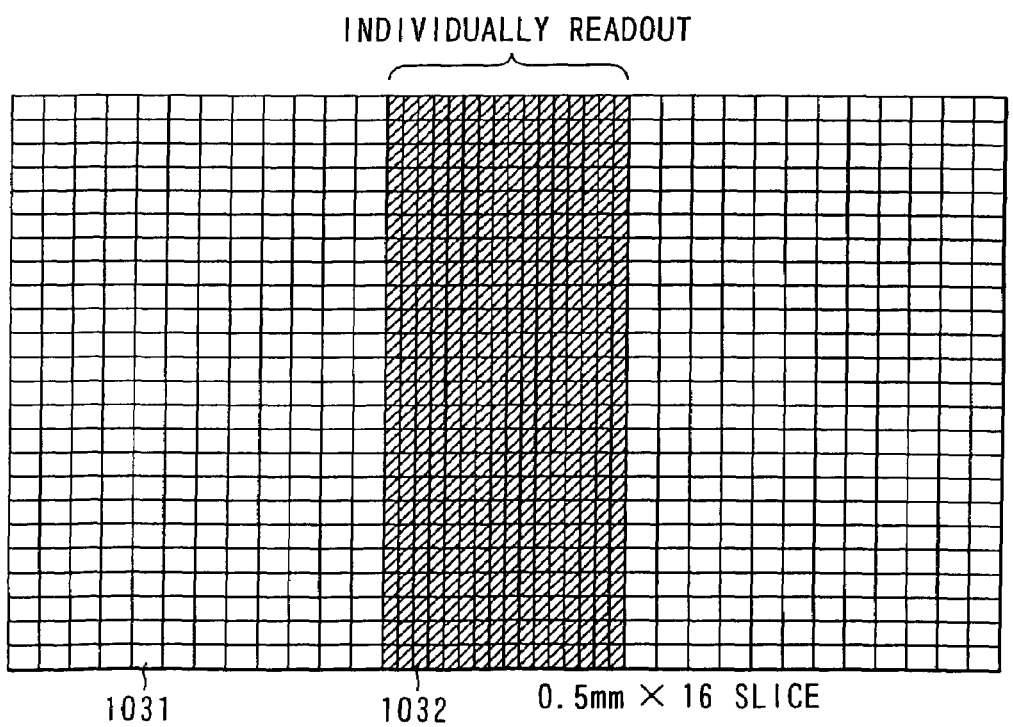
FIG. 13 is a plan view showing a plurality of photodiodes selected in accordance with a condition of slice thickness of 0.5 mm×16 slices in the seventh embodiment.
Figure 14:
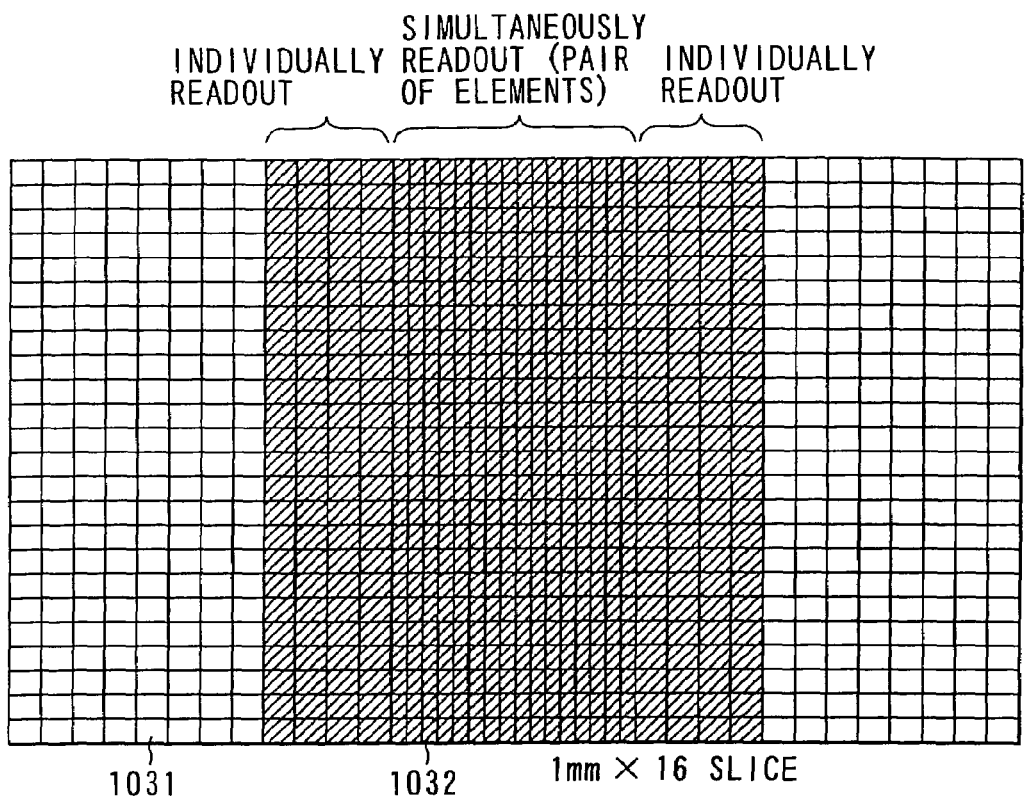
FIG. 14 is a plan view showing a plurality of photodiodes selected in accordance with a condition of slice thickness of 1 mm×16 slices in the seventh embodiment.
Figure 15:
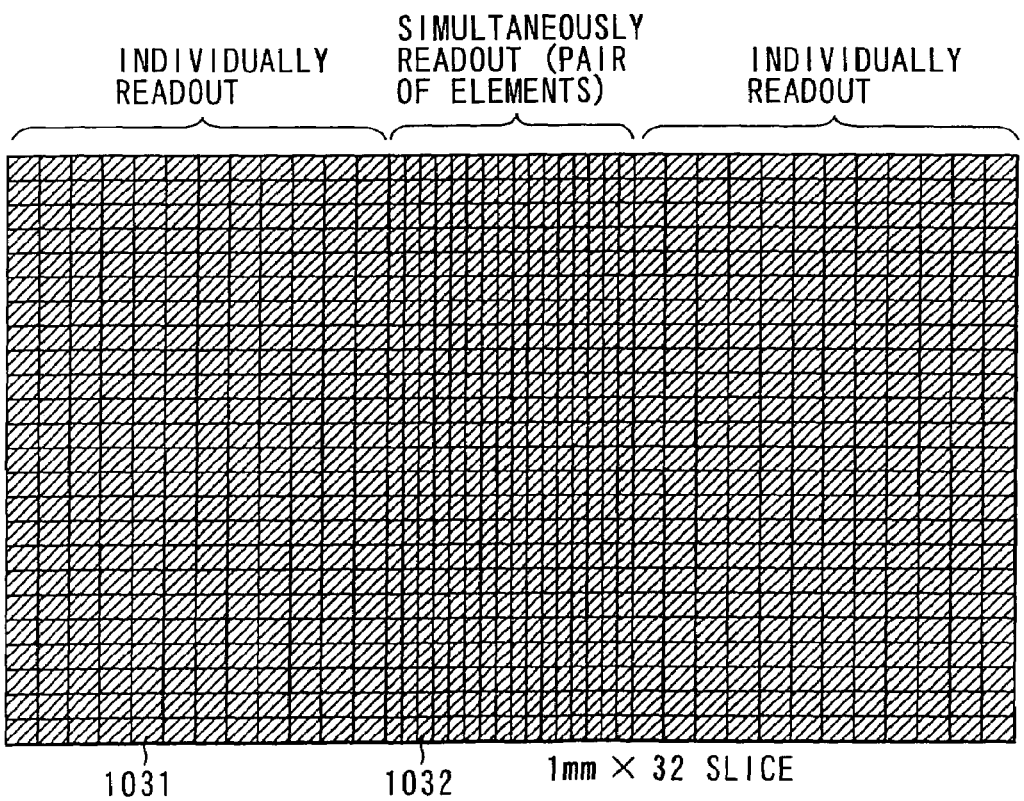
FIG. 15 is a plan view showing a plurality of photodiodes selected in accordance with a condition of slice thickness of 1 mm×32 slices in the seventh embodiment.
Figure 16:
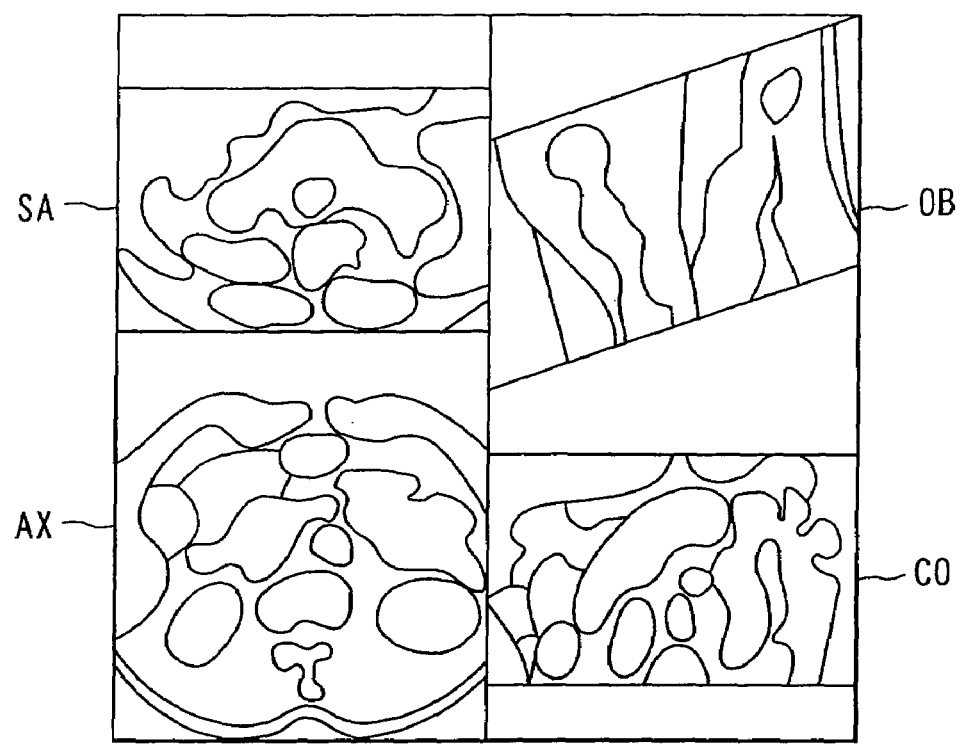
FIG. 16 is a view showing an example of how an axial tomographic image, sagittal tomographic image, and coronal tomographic image are displayed in the seventh embodiment.

Referring to FIG. 13, the detection elements used to image 16 0.5-mm thick slices are indicated by the hatching. Referring to FIG. 14, the detection elements used to image 16 1-mm thick slices are indicated by the hatching. Referring to FIG. 15, the detection elements used to image 32 1-mm thick slices are indicated by the hatching.

In imaging 16 0.5-mm thick slices, data from 16 0.5-mm thick tomographic images can be reconstructed acquired and by individually reading out electrical signals from the 0.5-mm wide detection elements 1032.

In imaging 16 1-mm thick slices, electrical signals are simultaneously read out from pairs of adjacent 0.5-mm wide detection elements 1032 so as to handle each pair as a single element. In addition, electrical signals are individually read out from four 1-mm wide detection elements 1031 on each of the two sides near the center line, i.e., a total of eight detection elements. With this operation, data from 16 1-mm thick tomographic images can be reconstructed acquired.

In imaging 32 1-mm thick slices, electrical signals are simultaneously read out from pairs of adjacent 0.5-mm wide detection elements 1032 so as to handle each pair as a single element. In addition, electrical signals are individually read out from the 1-mm wide detection elements 1032. With this operation, data from 32 1-mm thick tomographic images can be reconstructed can be acquired.

Obviously, the slice thickness can be changed to, for example, 2 mm or 3 mm by changing the signal readout method. In addition, the number of slices can be changed from 1 to 40. Furthermore, data with different slice thicknesses can be simultaneously acquired. Furthermore, data fot 8 slices having either of 0.5 mm, 1 mm, 2 mm, 3 mm and 4 mm slice thickness can be readout.

Such signal readout control can be realized by connecting a plurality of photodiodes on the same slice line to a single common signal line through a plurality of transistors and ON/OFF-controlling the transistors, as described in the first embodiment.

The above description is made on the mode of using the first detection element array group 1033 in imaging 0.5-mm thick slices. Instead of this mode, the mode of using only eight arrays of the first detection element array group 1033 in imaging 0.5-mm thick slices may be used. Various cases can be assumed in imaging slices with different thicknesses. In any case, the mode of using, for example, eight arrays or four arrays instead of 16 arrays may be used.

The 360° 2D projection data, i.e., 1,000 sets of 2D projection data, having undergone sensitivity correction, X-ray intensity correction, and the like in the preprocessing unit 106 is directly sent to the reconstructing unit 114. Alternatively, this data is temporarily stored in the storage unit 111 and then sent to the reconstructing unit 114, which performs reconstruction based on the data according to a reconstruction algorithm called the Feldkamp method.

The Feldkamp reconstruction method is an approximate reconstruction method that has been improved on the basis of the fan beam convolution backprojection method to generate 3D profile data to be referred to as volume data (a stereoscopic (3D) set of a plurality of voxel data) of X-ray absorption coefficients by handling a target area that is wide in the slice direction A as a set of a plurality of voxels. That is, in the Feldkamp reconstruction method, data is regarded as fan projection data to perform convolution, and backprojection is performed along an oblique ray in accordance with an actual cone angle with respect to a rotation center axis. According to the fan beam convolution backprojection method, which is not improved, since a ray is assumed to be perpendicular to the rotation center axis in backprojection, strong artifacts appear.

By using the Feldkamp reconstruction method, therefore, a detector which is wide in the slice direction can be effectively used.

The reconstructed volume data is sent to the data processing unit 113 directly or after temporarily stored in the storage unit 111. In accordance with an instruction from the operator, the data is converted into widely used image data, i.e., a tomographic image of an arbitrary slice, a projection image from an arbitrary direction, and so-called pseudo 3D image data such as a 3D surface image of a specific organ upon rendering, and then the resultant images are displayed on the display unit 116.

The operator can select and set an arbitrary display mode among the tomographic image of the arbitrary slice, the projection image from an arbitrary direction, the 3D surface image, and the like in accordance with the purpose of examination/diagnosis. In this case, therefore, images in different forms are generated from one volume data and displayed. In addition, the display modes includes the mode of simultaneously displaying a plurality of types of images. This mode and the mode of displaying one image can be switched in accordance with a purpose.

Note that the above "tomographic image of an arbitrary slice" includes tomographic images of slices perpendicular to an axial slice AX, e.g., a sagittal slice SA and coronal slice CO, and a tomographic image of an oblique slice OB that tilts with respect to the slice AX, SA, and CO, as well as a surface (axial slice) AX perpendicular to the body axis which is obtained by the conventional X-ray CT apparatus. These images are displayed by extracting voxel data of designated slices, which have designated thicknesses, from the volume data and binding them together.

In displaying the "projection image from an arbitrary direction", for example, the maximum value of voxel data arranged in the direction set as the arbitrary direction is picked up or the integral of the voxel data is calculated, and the resultant data is displayed as a 2D image. The method of displaying the "3D surface image" is a method of extracting a surface with a set threshold and displaying a 3D surface image by shadowing using a set light source. In this case, if the operator observes images while changing the threshold, he/she can grasp the internal structure.

As described above, the X-ray CT apparatus of this embodiment can acquire various images from one volume data, and the following effects can be obtained by using the radiation detector 103 according to the above description. The size of voxel data constituting the above volume data changes depending on the geometry of the system, data acquisition speed, and the like, and also greatly depends on the sizes of the detection elements 1031 and 1032 constituting the radiation detector 103. According to the radiation detector 103 of this embodiment, since a plurality of arrays (16 arrays) of narrow detection elements 1032 are prepared, for example, a resolution of about 0.5 mm×0.5 mm×0.5 mm can be attained at minimum with respect to voxel data, and relatively wide range can be imaged. That is, a wide imaging range and high resolution are maintained.

The radiation detector 103 according to this embodiment has a multi-array structure of the detection elements 1031 and 1032, and hence can obtain large volume data by one rotation. The radiation detector 103 can therefore acquire isotropic voxel data in a wide range. This makes it possible to make a tomographic image of an arbitrary slice have almost uniform resolution, thus obtaining a clinically useful image. Since isotropic voxel data can be acquired along all the axes, i.e., the X-axis, Y-axis, and Z-axis, diagnosis can be performed on the basis of images expressed with the same resolution as tomographic images of the axial slice AX, sagittal slice SA, and coronal slice CO. From a clinical viewpoint, so-called isotropic imaging based on 0.5-mm thick slices of the head portion and 1-mm thick slices of the abdominal portion can be implemented.

To allow "wide range" imaging is to allow "quick" imaging. This indicates that the total amount of radiation to which an object is exposed can be reduced. Besides this effect, according to the radiation detector 103 of this embodiment, since the number (or element count) of arrays of narrow detection elements 1031a is set to be smaller than that of arrays of wide detection elements 1031, there is no need to handle an enormous number of data unlike the case where a reduction in detection element size is made in the 2D array type detector disclosed in WO96/509896 like the one described in the "Description of the Related Art". From this viewpoint as well, "quick" processing can be performed. Obviously, the problem of "crosstalk" in this reference does not become a serious problem in this embodiment.

Furthermore, according to the radiation detector 103 of this embodiment, special effects can be obtained in imaging operation performed by continuously rotating the X-ray tube 101 and radiation detector 103.

According to scanning operation with one rotation, by performing the above data processing, as described above, one volume data without any time difference in the slice direction A can be obtained with respect to a wide target area in the slice direction A from 2D projection data from many directions which are obtained by only one rotation. Besides the axial slice AX, a tomographic image at a given time (the same time) can be observed. In this case, the form of a displayed image can be selected and set from a tomographic image of an arbitrary slice, a projection image from an arbitrary direction, 3D surface image, and the like, as described above.

According to continuous rotation scanning, when the same processing as that in one-rotation scanning is repeatedly performed with respect to 2D projection data from many directions which are obtained by a plurality of rotations, a plurality of volume data are obtained instead of one. Even if reconstruction is performed per rotation, sets equal in number to rotations can be obtained, and more volume data that slightly differ from each other with time can be obtained by shifting the range of data (the range of rotational angles of the system) used for reconstruction little by little.

Note that as in one-rotation scanning, the form of a displayed image in this continuous rotation scanning can be selected from a tomographic image of an arbitrary slice, a projection image from an arbitrary direction, 3D surface image, and the like.

Figure 17:
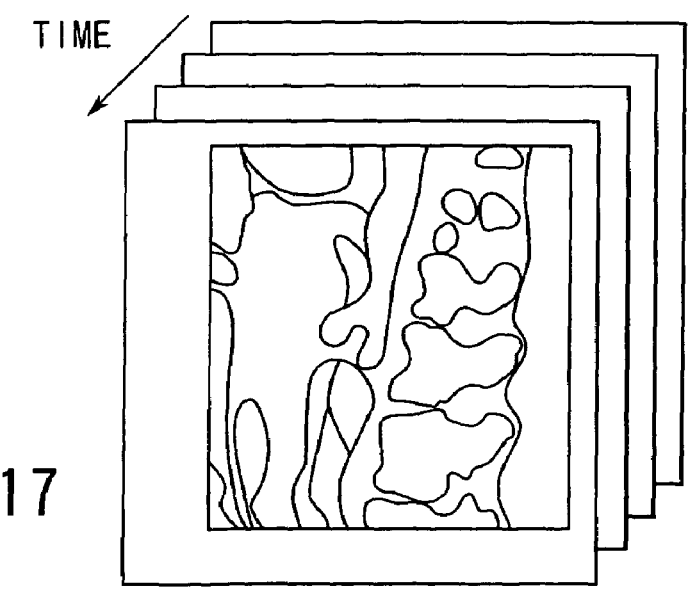
FIG. 17 is a view showing an example of how moving images are displayed in the seventh embodiment.

If images in the set display form which slightly change with time are generated from the volume data that slightly differ from each other with time, and the generated images are sequentially displayed, the operator can observe the images as moving images in real time, as shown in FIG. 17. That is, images can be displayed as moving images concurrently with continues scanning.

Data processing in this continuous rotation scanning will be further described below. In the following description, the angle range of projection data required to reconstruct one 3D image data is 360°. However, as described above, for example, the angle range may be 180°+view angle instead of 360°.

First of all, the X-ray tube 101 continuously rotates around the object at high speed, together with the radiation detector 103. The time required per rotation is t0 (1 sec in the above case). Sequentially acquired projection data are subjected to preprocessing almost in real time. The reconstructing unit 114 reconstructs volume data "I" on the basis of preprocessed 360° projection data. The data processing unit 113 then generates image data "DI", e.g., a tomographic image of an arbitrary slice, a projection image from an arbitrary direction, or 3D surface image, on the basis of the reconstructed volume data I. This image data "DI" is displayed on the display unit 116.

When moving images are to be displayed in the above manner, a series of operations from scanning to image display are concurrently performed in the respective scanning operations from the first scanning operation to the nth scanning operation (for example, the second scanning operation is executed concurrently with reconstruction processing based on the first scanning operation). Images are sequentially reconstructed on the basis of 2D projection data continuously obtained by the above processing, and are sequentially displayed.

For this purpose, the reconstructing unit 114 has the processing ability required to reconstruct the volume data I within a time shorter than the time t0 required to acquire projection data corresponding to a predetermined angle range (360° in this case) concurrently with 2D projection data acquiring operation (scanning). The data processing unit 113 has the processing ability required to generate the image data DI from the volume data I within a time shorter than the reconstruction time required for the volume data I.

The display unit 116 is quipped with a counter, a memory, and the like which are required to start displaying the image data DI a predetermined time after a start point Ts or end point Te of the period of acquiring operation for projection data from which the image data DI originates.

Obviously, with regards to the above point, the signal processing ability associated with the radiation detector 103 is required to be high. According to the radiation detector 103 in this embodiment, since "quick" signal processing can be performed as described above, this processing greatly contributes to smooth execution of moving image display like that described above.

In the above embodiment, data processing such as reconstruction and slice conversion and display operation are performed within an X-ray CT apparatus 100 (such a form of operation is general). Instead of this form of operation, in the present invention, these data processes and the like may be executed by the external image processing unit 200 in FIG. 1. When this external image processing unit 200 is to be used, the data sent from the X-ray CT apparatus 100 to the image processing unit 200 does not impair the effects of the above embodiment in any state, e.g., before reconstruction, after reconstruction, or immediately before display after data processing.

According to the above description, a tomographic image of an arbitrary slice, a projection image from an arbitrary direction, a 3D surface image, and the like can be displayed. According to the present invention, in addition to this effect, information that changes with time such as the CT value of an ROI or electrocardiogram may be displayed in a graph, together with these main images, and the time of each main image displayed on the graph may also be displayed.

This embodiment can be variously modified. For example, the above embodiment may be applied to helical scanning operation in which at least the gantry or bed is moved during scanning such that the X-ray tube 101 lays down a helical trail around the object. At this time, volume data constituted by isotropic voxel data can be obtained by setting imaging conditions to optimal values, which include at least one of a detection element array used for data acquisition, helical pitch, scanning range, scanning time, and tube current. In implementing this isotropic imaging, data acquisition is preferably performed by using only the first detection element array with a small detection width from the viewpoint of high resolution. For example, imaging conditions are set as follows: the diameter of an imaging area head portion: 18 cm; the number of 0.5-mm detection element arrays: 4; helical pitch: 3; scanning range: 60 mm; scanning time: 20 sec; tube current: 150 mAs; and the reconstruction pitch: 0.3 mm.

And, the arrangement of the detection element and the structure of the detection vessel were combined with first- the 6th embodiments either or the option.

Eighth Embodiment

Figure 18:
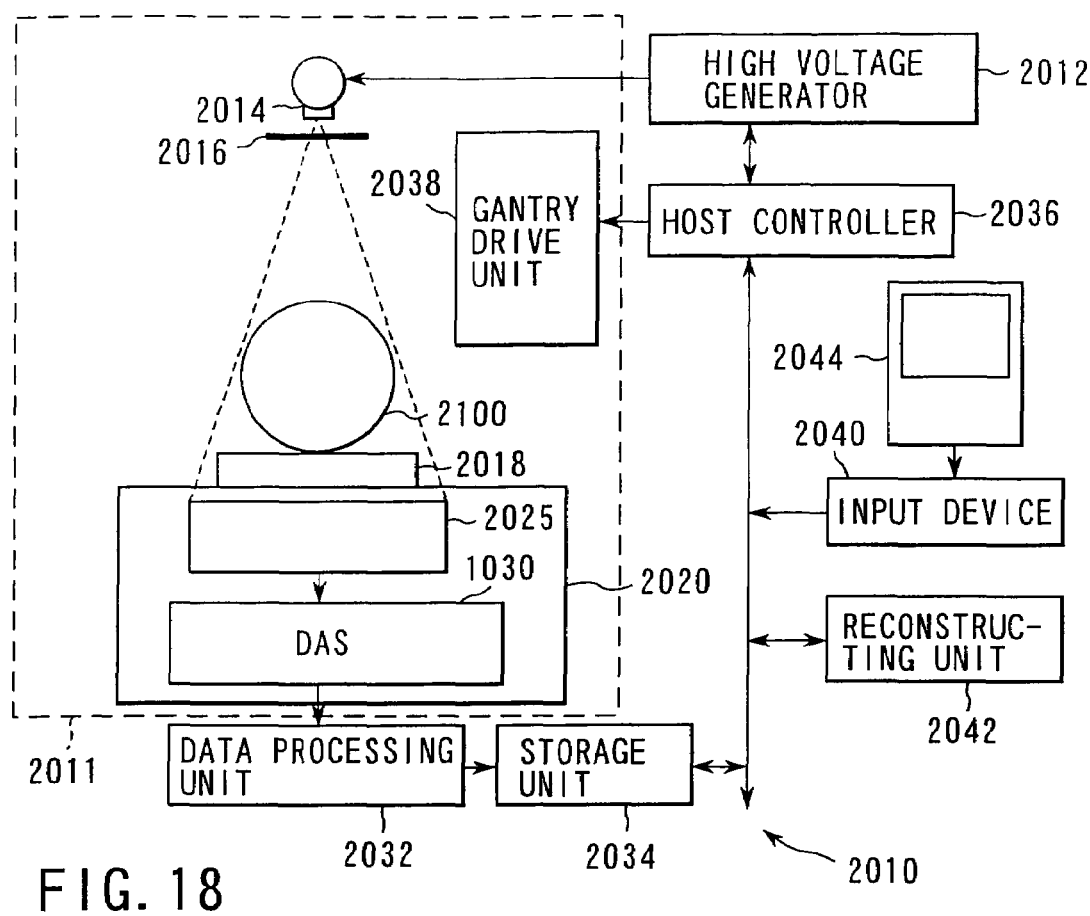
FIG. 18 is a block diagram showing the arrangement of an X-ray CT apparatus according to the eighth embodiment.

FIG. 18 shows the schematic arrangement of an X-ray CT apparatus according to the eighth embodiment. Referring to FIG. 18, an X-ray CT apparatus 2010 is comprised of a gantry 2011 for acquiring projection data of an object to be examined and a data processing system for performing image reconstruction processing, reconstructed image display, and the like on the basis of acquired projection data.

The gantry 2011 includes an X-ray tube 2014, a slit 2016, a bed 2018 on which the object lies, a diagnosis opening portion in which the object is inserted for diagnosis, a gantry drive unit 2038, and a radiation detecting system 2020.

The X-ray tube 2014 is a vacuum tube for generating X-rays. The X-ray tube 2014 accelerates electrons by the high voltage generated by a high voltage generator 2012 and makes the electrons collide with a target, thereby generating X-rays.

The slit 2016 is formed between the X-ray tube 2014 in the gantry 2011 and the object to shape X-ray cone beam emitted from the X-ray focal point of the X-ray tube 2014 so as to form an X-ray beam having a predetermined solid angle.

The bed 2018 can be driven to slide along the body axis of the object by a bed drive unit.

The gantry drive unit 2038 performs drive control, e.g., rotating the X-ray tube 2014 and radiation detecting system 2020 together around a center axis parallel to the body axis of the object inserted into the diagnosis opening portion.

The radiation detecting system 2020 is a system made up of a radiation detector 2025 and data acquisition system (to be referred to as a DAS hereinafter) 2030. The radiation detector 2025 is constituted by a plurality of arrayed detector modules. Since a conventional detector has a resolution of about 0.5 to 1 mm in the channel direction, it suffices if the radiation detecting system 2020 according to this embodiment has the same resolution in the slice direction as that in the channel direction. That is, the following description is made on the premise that a 0.5-mm thick slice is a slice having the minimum imaging slice thickness. The DAS 2030 is comprised of a plurality of DAS chips, performs amplification processing and A/D conversion processing for X-ray transmission data sent from the radiation detector 2025 and control operation for binding the data into data having a predetermined slice thickness, and sends out the resultant data to a data processing unit 2032. Note that a DAS chip may be sometimes called a DAM-ASSY.

In addition, the radiation detecting system 2020 according to this embodiment has the following characteristic feature to greatly reduce noise.

The data processing system includes the high voltage generator 2012, the data processing unit 2032, a storage unit 2034, a host controller 2036, an input device 2040, a reconstructing unit 2042, and a display unit 2044.

The high voltage generator 2012 is a unit for applying a high voltage to the X-ray tube 2014, and is comprised of a high voltage transformer, filament heating converter, rectifier, high voltage switch, and the like. This high voltage generator 2012 applies a high voltage to the X-ray tube 2014 by using, for example, a contact type slip ring mechanism.

The host controller 2036 is equipped with a computer circuit having a CPU and connected to the high voltage generator 2012. The host controller 2036 is also connected to the bed drive unit (not shown), gantry drive unit 2038, and radiation detecting system 2020 in the gantry 2011 through a bus. In addition, the host controller 2036, data processing unit 2032, storage unit 2034, reconstructing unit 2042, display unit 2044, and input device 2040 are connected to each other through a bus, and can exchange image data and control data at high speed through the bus.

The host controller 2036 executes, for example, the following control to perform acquisition processing for X-ray transmission data (projection data). More specifically, the host controller 2036 stores scanning conditions such as a slice thickness, input from the operator through the input device 2040, in the internal memory, and drives the high voltage generator 2012, bed drive unit, and gantry drive unit 2038 while controlling the high voltage generator 2012, the bed drive unit, the gantry drive unit 2038, and the feed amount and speed of the bed 2018 in the body axis direction, the rotational speed and pitch of the gantry 2011 (the X-ray tube 2014 and radiation detecting system 2020), irradiation timing of X-rays, and the like. As a consequence, a desired imaging area of the object is irradiated with X-ray cone beams from many directions, and the transmission X-rays transmitted through the imaging area of the object can be detected as X-ray transmission data through the respective detection elements of the radiation detecting system 2020.

At the same time, the host controller 2036 ON/OFF-controls the switching elements of the radiation detecting system 2020 on the basis of the scanning conditions (or scanning conditions in the manual mode) stored in the internal memory. The host controller 2036 switches the connected states of the respective detection elements (photodiodes) of the radiation detecting system 2020 and the DAS and combines the X-ray transmission data detected by the respective detection elements in a predetermined unit. The host controller 2036 then sends out the resultant data as X-ray transmission data of a plurality of slices corresponding to the scanning conditions, and executes predetermined processing.

The data processing unit 2032 is equipped with a computer circuit having a CPU and the like and holds 16-slice projection data acquired by the respective DAS chips of the radiation detecting system 2020. The data processing unit 2032 performs addition processing for all the projection data of the same slice obtained from many directions by rotation of the gantry 2011 described above and performs interpolation processing, correction processing, and the like for multi-direction data obtained by the addition processing, as needed.

The storage unit 2034 stores data and the like required for data processing in the data processing unit 2032.

The reconstructing unit 2042 performs reconstruction processing for the projection data, obtained by data processing by the data processing unit 2032, according to the Feldkamp reconstruction method, thereby generating 16-slice reconstructed image data.

The display unit 2044 displays the reconstructed image data generated by the reconstructing unit 2042.

The input device 2040 includes a keyboard, various switches, mouse, and the like, and allows the operator to input various scanning conditions such as a slice thickness and slice count.

The reconstructing unit 2042 has a large-capacity secondary storage unit capable of storing the generated reconstructed image data.

The radiation detecting system 2020 according to this embodiment will be described in detail below.

Each detector module of the radiation detecting system 2020 is constituted by one detector block and one DAS block. That is, one detector block and one DAS block constitute a detector module. The radiation detector section 2020 is formed by arraying the detector modules in the channel direction. The respective constituent elements of the radiation detecting system 2020 will be sequentially described below.

Detector Module and Radiation Detector

Figure 20A:
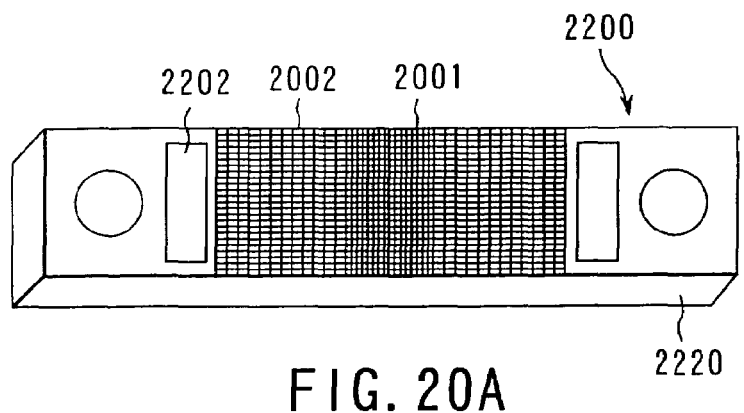
FIG. 20A is a perspective view of a detector block forming one detector module in FIG. 19.

FIG. 20A is a plan view of a detector block 2200. The detector block 2200 is formed by mounting a photodiode chip 2201 and switching chip 2202 on a rigid multilayer wiring board 2220. The photodiode chip 2201 converts light, converted from X-rays by a scintillator, into an electrical signal by using a plurality of photodiodes and outputs the signal. The switching chip 2202 is made of CMOS (Complementary MOS) elements for binding acquired X-ray transmission data in a predetermined unit and sending out the resultant data to the DAS chips. A connector electrically connected to the switching chip 2202 is attached to the lower surface of the multilayer wiring board 2220.

Figure 19:
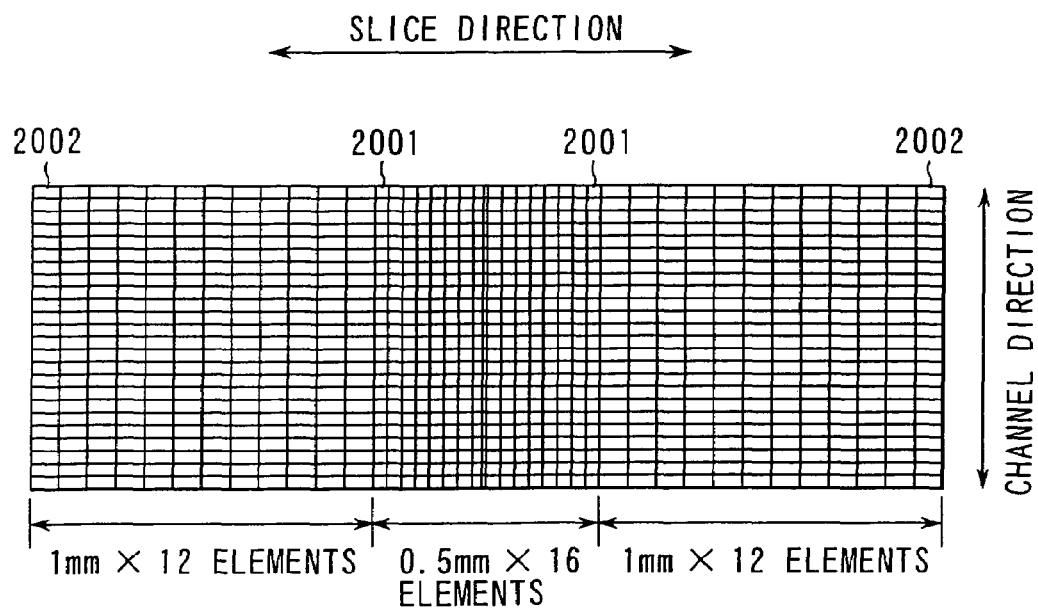
FIG. 19 is a plan view of a plurality of detector modules constituting the radiation detector in FIG. 18.

FIG. 19 is a developed view of the photodiode chip 2201. As shown in FIG. 19, the photodiode chip 2201 has a plurality of photodiodes 2001 and 2002. One photodiode 2002 has a sensitivity range 1 mm square in the channel direction and a sensitivity range 1 mm square in the slice direction. The other photodiode 2001 has a sensitivity range 1 mm square in the channel direction, like the photodiode 2002, and a sensitivity range 0.5 mm square in the slice direction, which is ½ that of the photodiode 2002.

The 16 0.5-mm wide photodiodes 2001 are arrayed in the slice direction. The 48 0.5-mm wide photodiodes 2001 are arrayed in the channel direction. The 12 1-mm wide photodiodes 2002 are arrayed on each of two sides of the 0.5-mm wide photodiode 2001 in the slice direction. Likewise, the 48 1-mm wide photodiodes 2002 are arrayed in the channel direction.

DAS Block and Data Acquisition System

Figure 20B:
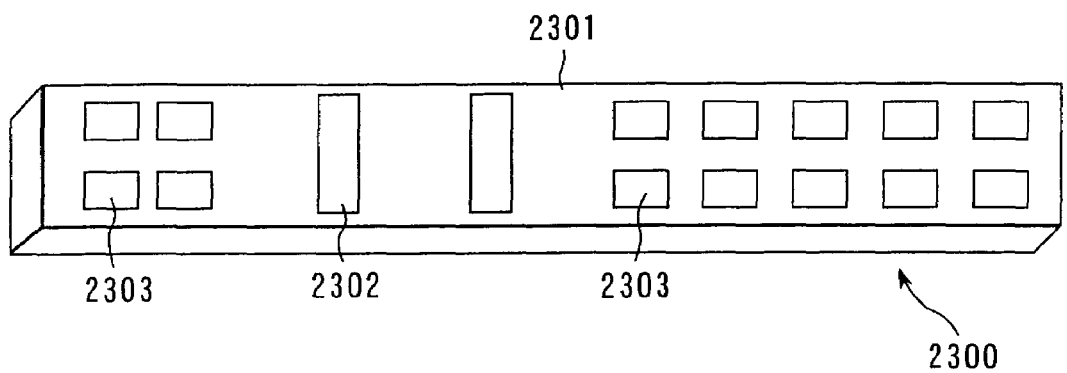
FIG. 20B is a perspective view of a DAS block forming one detector module in FIG. 19.

FIG. 20B is a plan view of a DAS block 2300. The DAS block 2300 has a rigid printed wiring board 2301. A connector 2302 detachably connected to a connector formed on the lower surface of the detector block 2200 is formed on the upper surface of the printed wiring board 2301. A plurality of DAS chips 2303 are mounted on the printed wiring board 2301.

Detector Module and Radiation Detector

A detector module 2022 will be described next.

Figure 20C:
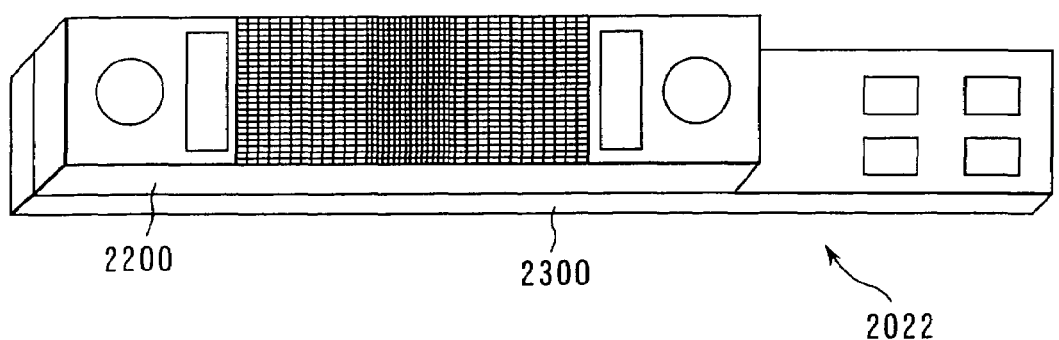
FIG. 20C is a perspective view of the detector module in FIG. 19.

FIG. 20C is a plan view of the detector module 2022. As shown in FIG. 20C, the detector module 2022 is comprised of one detector block 2200 and one DAS block 2300. The detector block 2200 and DAS block 2300 are fixed and electrically connected to each other through the connector 2302. The DAS block 2300 acquires the X-ray image data detected by the detector block 2200 connected to the connector 2302. That is, one detector module 2022 forms an independent system for detecting and acquiring data. The radiation detecting system 2020 is formed by arraying a plurality of detector modules 2022, each shown in FIG. 20C, along the channel direction.

If one of the detector block 2200 and DAS block 2300 coupled to each other fails, the faulty block can be replaced with a normal block by separating them.

FIG. 21A is a sectional view of the detector module 2022. The detector module 2022 relays the detector block 2200 to the DAS block 2300 with a rigid printed wiring board 2210. The detector block 2200 is mounted on the upper surface of the relay board 2210 through a connector 2214, and the DAS block 2300 is mounted outside the X-ray irradiation area on the lower surface through the connector 2302. As shown in FIG. 21B, the DAS block 2300 may be mounted outside the X-ray irradiation range on the upper surface of the relay board 2210.

By placing the DAS block 2300 outside the X-ray irradiation range in this manner, a DAS operation error due to the ionization effect of X-rays can be prevented.

Figure 22:
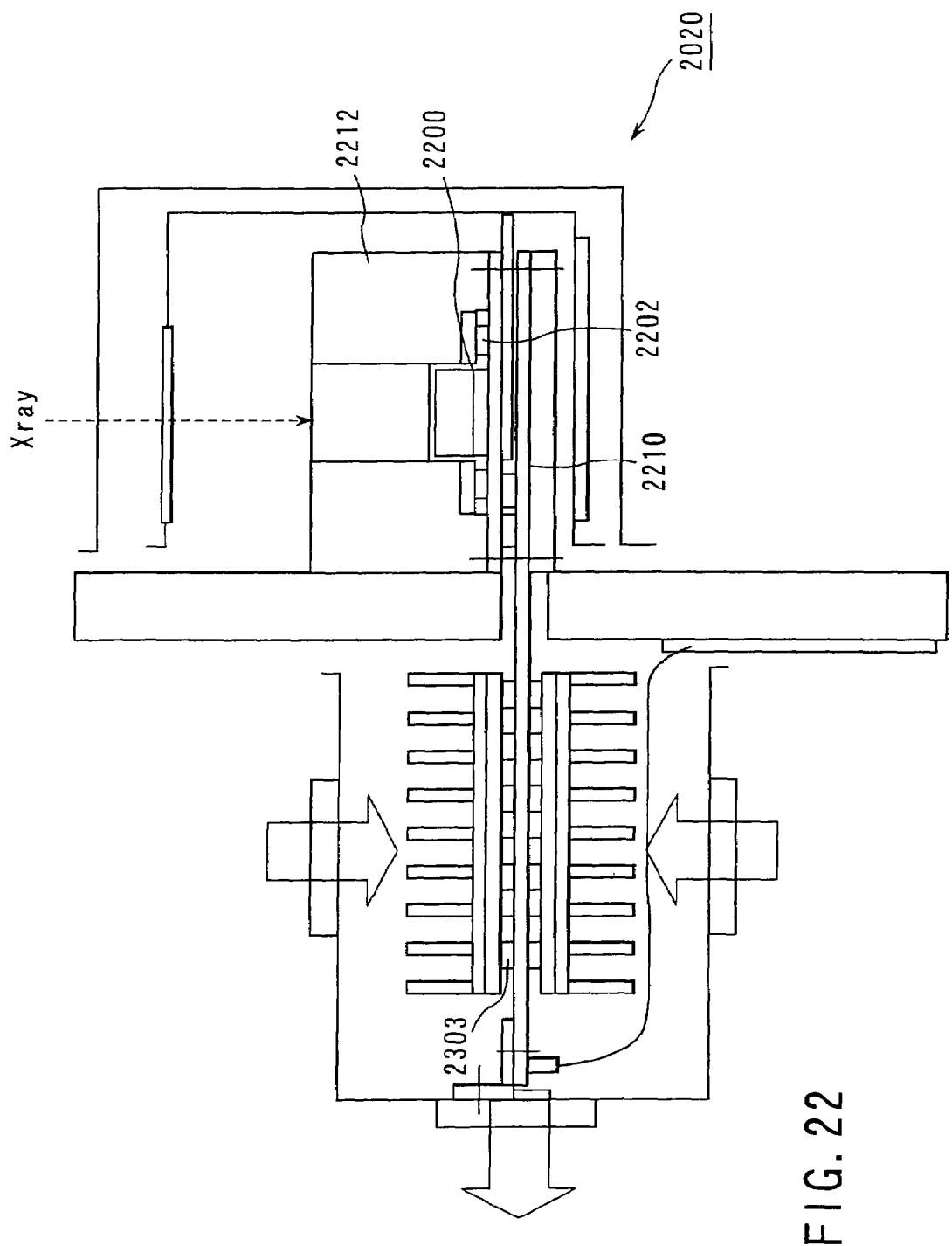
FIG. 22 is a sectional view of a DAS block in FIG. 21A.

FIG. 22 is a sectional view of the detector module 2022 with the DAS blocks 2300 mounted on the upper and lower surfaces of the relay board 2210. The detector module 2022 shown in FIG. 22 includes a support 2212 for arraying a plurality of detector blocks 200, a radiator fin/pin 2320 for radiating heat from the DAS chips 2303, a heat conducting rubber member 2322 for connecting the radiator fin/pin 2320 to the DAS chips 2303, a fan 2324 for cooling the data acquisition system 2030.

FIG. 23A is a cross-sectional view of the detector module 2022. The detector module 2022 is formed by stacking the detector block 2200, DAS block 2300, and rigid relay board 2210 made of a ceramic or glass epoxy resin material. The detector block 2200 is formed by stacking the scintillator 2201, a photodiode 2204, and the switching chip 2202. Note that the DAS block 2300 is obtained by encapsulating a predetermined number of DAS chips 2303 with a resin. The scintillator 2201 and photodiode 2204 are encapsulated with a resin 2206.

Since the detector module 2022 is formed by stacking the DAS block 2300, relay board 2210, and detector block 2200, the apparatus size can be reduced. In this case, the DAS block 2300 exists in the X-ray irradiation area. Therefore, a lead member is preferably placed on the X-ray incident side of each DAS chips 2303.

In addition, since the detector module 2022 is placed outside the X-ray irradiation area on the DAS block 2300, an operation error due to the ionization effect of X-rays can be prevented.

Figure 24A:
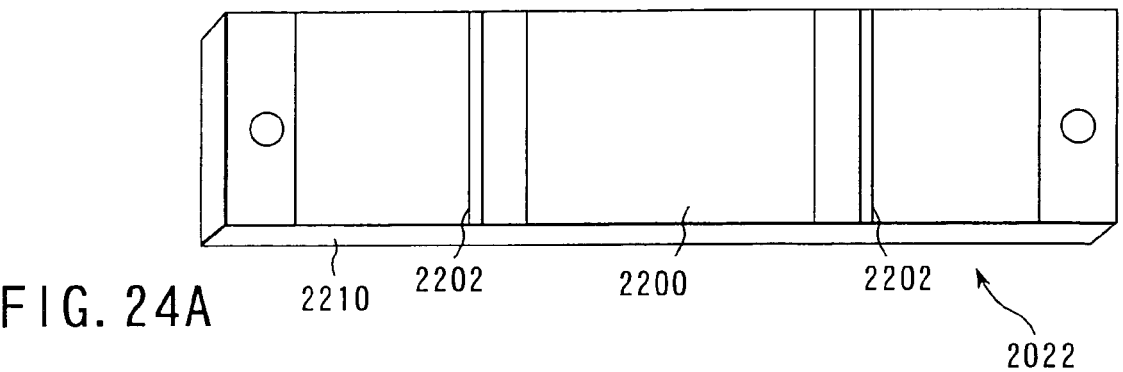
FIG. 24A is a top view of a detector module according to the eighth embodiment.
Figure 24B:
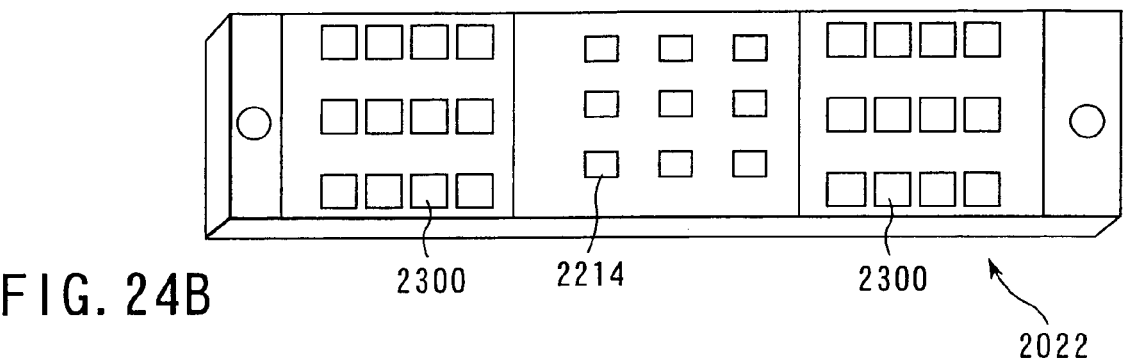
FIG. 24B is a rear view of the detector module according to the eighth embodiment.

Obviously, the assumed positions of the detector block 2200 and DAS block 2300 are not specifically limited. For example, the detector block 2200 may be placed in the central portion of the relay board 2210 as shown in FIG. 24A, and the DAS block 2300 may be placed on a peripheral portion of the relay board 2210 as shown in FIG. 24B.

The following effects can be obtained by this embodiment.

First, since the detector block 2200 and DAS block 2300 are commonly mounted on the rigid board, vibrations of the flexible PC board and disconnection of the connector due to rotation in scanning operation can be prevented as well as the occurrence of noise due to the antenna effect and the like of the flexible PC board. Since no flexible PC board is used, a shield for noise reduction can be easily mounted. As a consequence, noise can be greatly reduced as compared with the prior art.

Second, since the detector block and DAS block are connected through the connector, only a small space is required for connection between units. This makes it possible to reduce the apparatus size. In addition, since connection using the connector facilitates connection between units and disconnection from each other, replacement of units can be easily performed as compared with bump connection.

Third, since the detector modules and DAS blocks are arranged in one-to-once correspondence, for example, replacement of only some units can be easily performed. Therefore, the overall data acquisition system need not be replaced. This makes it possible to reduce the running cost.

Ninth Embodiment

Figure 25:
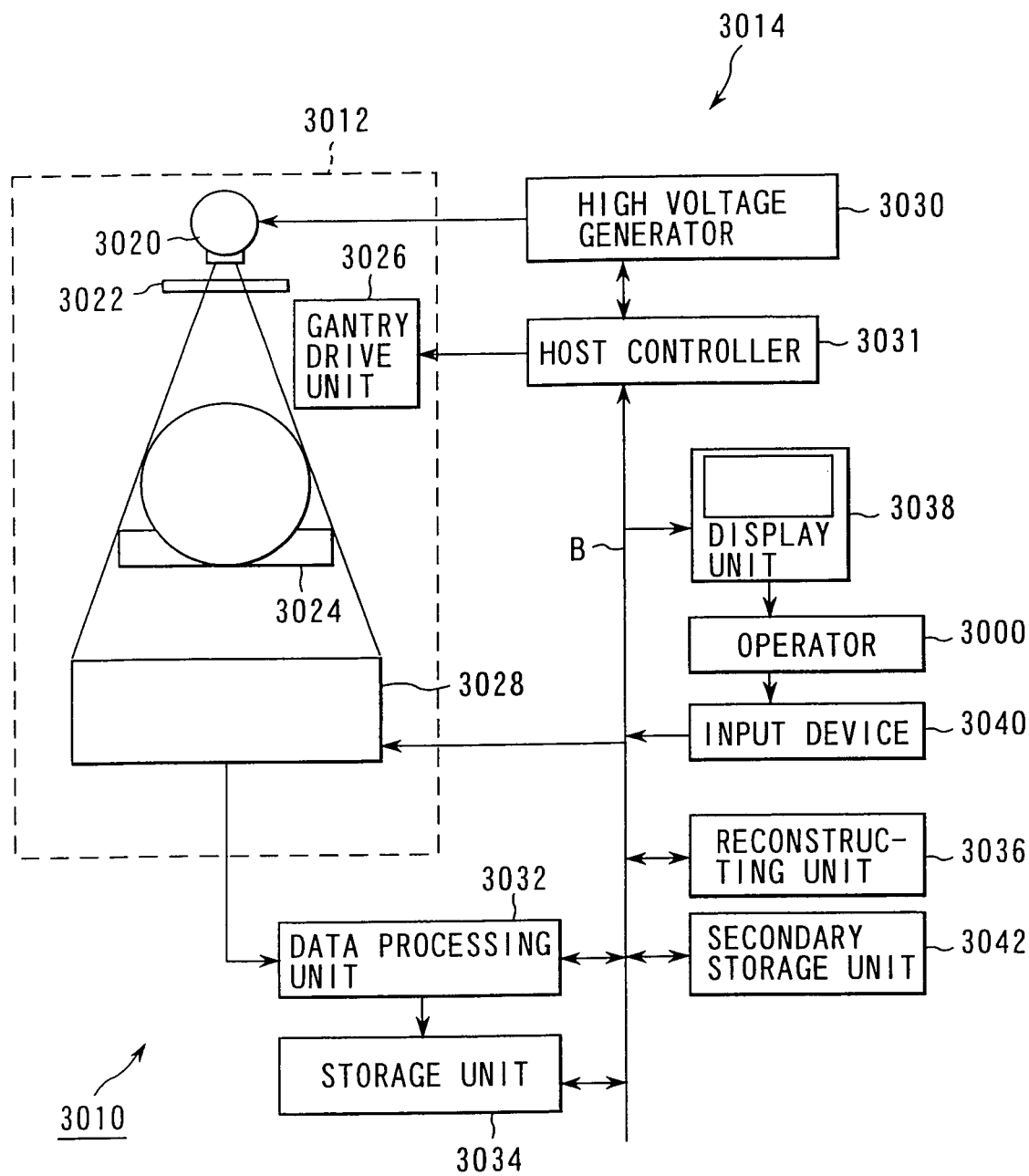
FIG. 25 is a block diagram showing an X-ray CT apparatus according to the ninth embodiment.

FIG. 25 shows the arrangement of an X-ray CT apparatus according to the ninth embodiment. An X-ray CT apparatus 3010 is comprised of a gantry 3012 for acquiring projection data of an object to be examined and a system unit 3014 for performing image reconstruction processing and reconstructed image display on the basis of acquired projection data.

The gantry 3012 includes an X-ray tube 3020, a slit 3022, a bed 3024 on which an object lies, a diagnosis opening portion in which the object is inserted for diagnosis, a gantry drive unit 3026, and a radiation detector 3028.

The X-ray tube 3020 is a vacuum tube for generating X-rays. The X-ray tube 3024 accelerates electrons by the high voltage generated by a high voltage generator 3030 and makes the electrons collide with a target, thereby generating X-rays.

The slit 3022 is formed between the X-ray tube 3020 in the gantry 3012 and the object to shape X-ray cone beam emitted from the X-ray focal point of the X-ray tube 3020 so as to form an X-ray beam having a predetermined solid angle.

The bed 3024 can be driven to slide along the body axis of the object by a bed drive unit (not shown).

The gantry drive unit 3026 performs drive control, e.g., rotating the X-ray tube 3020 and radiation detector 3028 together around a center axis parallel to the body axis of the object inserted into the diagnosis opening portion.

The radiation detector 3028 is formed by arraying a plurality of detector modules in the channel direction.

The system unit 3014 includes the high voltage generator 3030, a host controller 3031, a data processing unit 3032, a storage unit 3034, a reconstructing unit 3036, a display unit 3038, an input device 3040, and a secondary storage unit 3042.

The high voltage generator 3030 is a unit for applying a high voltage to the X-ray tube 3020, and is comprised of a high voltage transformer, filament heating converter, rectifier, high voltage switch, and the like. This high voltage generator 3030 applies a high voltage to the X-ray tube 3020 by using, for example, a contact type slip ring mechanism.

The host controller 3031 is equipped with a computer circuit having a CPU and connected to the high voltage generator 3030. The host controller 3031 is also connected to the bed drive unit (not shown), gantry drive unit 3026, and radiation detector 3028 in the gantry 3012 through a bus B. In addition, the host controller 3031, data processing apparatus 3032, storage unit 3034, reconstructing unit 3036, display unit 3038, input device 3040, and secondary storage unit 3042 are connected to each other through the bus B, and can exchange image data and control data at high speed through the bus B.

The host controller 3031 executes, for example, the following control to perform acquisition processing for X-ray transmission data (projection data). More specifically, the host controller 3031 stores scanning conditions such as a slice thickness, input from an operator 3000 through the input device 3040, in the internal memory, and drives the high voltage generator 3030, bed drive unit (not shown), and gantry drive unit 3026 while controlling the high voltage generator 3030, the bed drive unit (not shown), the gantry drive unit 3026, and the feed amount and speed of the bed 3024 in the body axis direction, the rotational speed and pitch of the gantry 3012 (the X-ray tube 3020 and radiation detector 3028), irradiation timing of X-rays, and the like. As a consequence, a desired imaging area of an object P is irradiated with X-ray cone beams from many directions, and the transmission X-rays transmitted through the imaging area of the object can be detected as X-ray transmission data through the respective detection elements of the radiation detector 3028.

At the same time, a host controller 3025 ON/OFF-controls the switches of the radiation detector 3028 on the basis of the scanning conditions (or scanning conditions in the manual mode) stored in the internal memory. The host controller 3025 switches the connected states of the respective detection elements (photodiodes) of the radiation detector 3028 and the DAS and combines the X-ray transmission data detected by the respective detection elements in a predetermined unit. The host controller 3025 then sends out the resultant data as X-ray transmission data of a plurality of slices corresponding to the scanning conditions, and executes predetermined processing.

The data processing unit 3032 is equipped with a computer circuit having a CPU and the like and holds 32-slice projection data acquired by the respective data acquisition elements of the radiation detector 3028. The data processing unit 3032 performs addition processing for all the projection data of the same slice obtained from many directions by rotation of the gantry 3012 described above and performs interpolation processing, correction processing, and the like for multi-direction data obtained by the addition processing, as needed.

The storage unit 3034 stores data and the like required for data processing in the data processing unit 3032.

The reconstructing unit 3036 performs reconstruction processing for the projection data, obtained by data processing by the data processing unit 3032, according to the Feldkamp reconstruction method to generate 8-slice reconstructed image data.

The display unit 3038 displays the reconstructed image data generated by the reconstructing unit 3036.

The input device 3040 includes a keyboard, various switches, mouse, and the like, and allows the operator to input various scanning conditions such as a slice thickness and slice count.

The secondary storage unit 3042 is a unit having large-capacity storage area capable of storing the reconstructed image data generated by the reconstructing unit 3036.

Figure 26A:
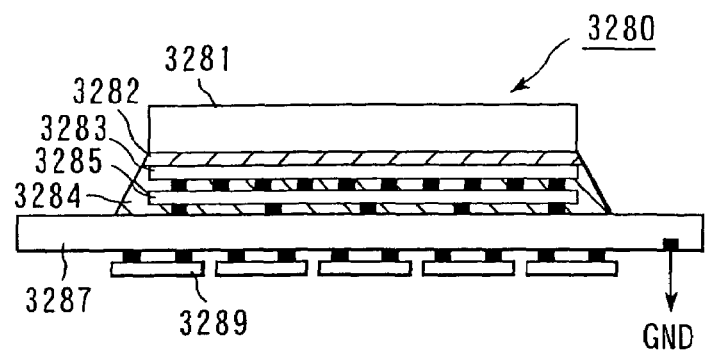
FIG. 26A is a sectional view of an X-ray detector module according to the ninth embodiment.

FIG. 26A is a sectional view of a detector module 3280. A photodiode chip 3283 is mounted on the lower surface of a scintillator 3281 and is fixed thereto with an adhesive 3282. A switching chip 3285 is bump-connected to the lower surface of the photodiode chip 3283. The switching chip 3285 is mounted on the upper surface of a rigid multilayer wiring board 3287. The switching chip 3285 is electrically connected to the multilayer wiring board 3287 through solder bumps. The multilayer structure made up of the photodiode chip 3283, switching chip 3285, and multilayer wiring board 3287 is encapsulated with a resin 3284.

DAS chips 3289 are mounted on the lower surface of the multilayer wiring board 3287. The multilayer wiring board 3287 is electrically connected to the DAS chips 3289 by flip chip bonding.

Figure 27:
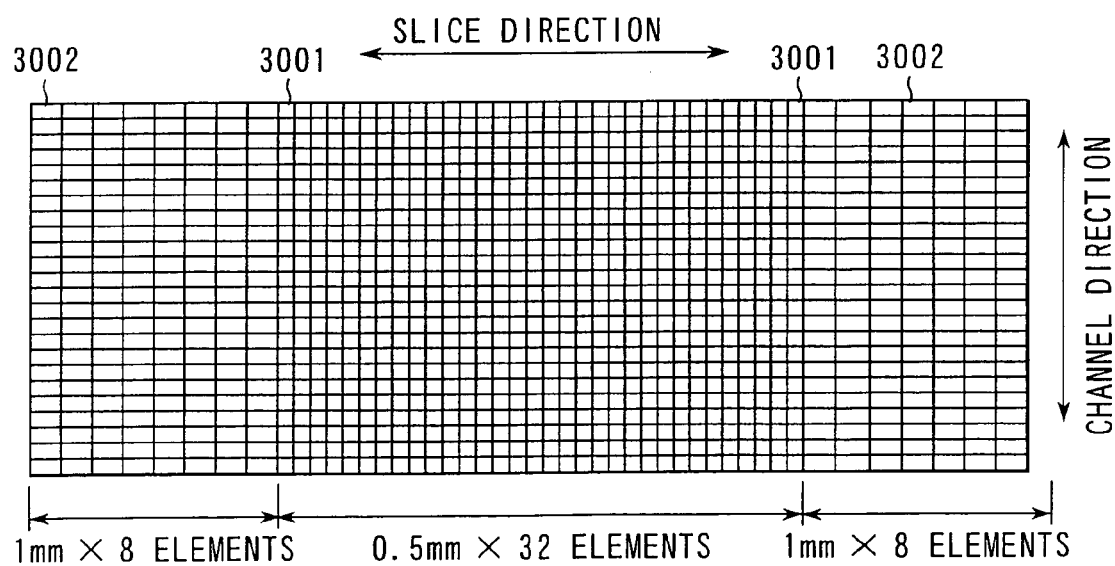
FIG. 27 is a plan view of an X-ray detector module according to the ninth embodiment.

FIG. 27 is a developed view of the photodiode chip 3283. The photodiode chip 3283 has a plurality of photodiodes 3001 and 3002. One photodiode 3002 has a sensitivity range 1 mm square in the channel direction and a sensitivity range 1 mm square in the slice direction. The other photodiode 3001 has a sensitivity range 1 mm square in the channel direction, like the photodiode 3002, and a sensitivity range 0.5 mm square in the slice direction, which is ½ that of the photodiode 3002.

The 32 0.5-mm wide photodiodes 3001 are arrayed in the slice direction. The 48 0.5-mm wide photodiodes 3001 are arrayed in the channel direction. The 8 1-mm wide photodiodes 3002 are arrayed on each of two sides of the 0.5-mm wide photodiode 3001 in the slice direction. Likewise, the 48 1-mm wide photodiodes 3002 are arrayed in the channel direction.

The scintillator 3281 is made up of 0.5-mm wide scintillator elements and 1-mm wide scintillator elements arranged in the same pattern as that of the photodiodes 3001 and 3002. Lead separators are inserted between the adjacent scintillators to prevent crosstalk.

Each scintillator has a box-like shape (hexahedron), and has reflective agent layers (not shown) formed on its X-ray incident surface and an end face in the slice thickness direction. A photodiode is joined to the fluorescence output surface (opposite to the X-ray incident surface) of each scintillator with a joining member such as the adhesive 3282 to receive fluorescence.

Referring back to FIG. 26A, the photodiode chip 3283 is comprised of photodiodes equal in number to the scintillator elements. The photodiodes and scintillator elements are connected in one-to-once correspondence with each other optically. Each photodiode has an active area (sensitivity range), and converts the light received through the active area into an electrical signal.

The switching chip 3285 has a plurality of CMOS (Complementary MOS) transistors. The plurality of transistors are connected to the plurality of photodiodes. The electrical signals generated by the photodiodes are supplied to the DAS chips 3289 through the corresponding transistors.

The multilayer wiring board 3287 is made of a plurality of thin printed wiring boards each having via holes. At least one thin printed wiring board has an X-ray shield function.

Each DAS chip 3289 performs amplification processing and A/D conversion processing for the electrical signal sent through the switching chip 3285.

Figure 26B:
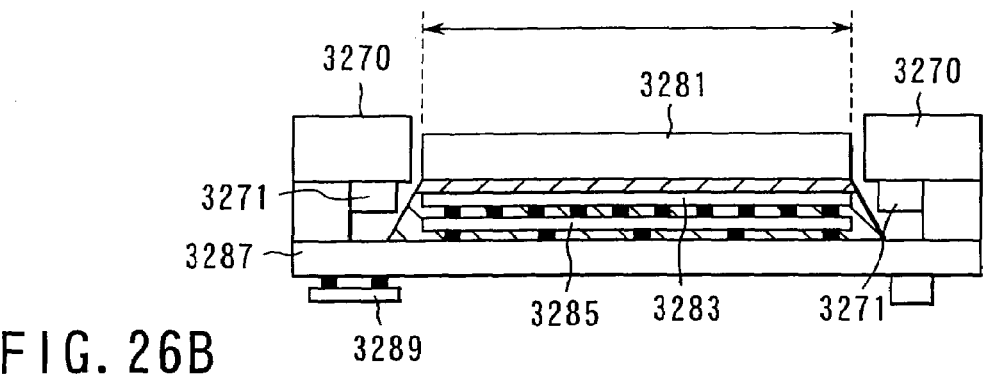
FIG. 26B is a sectional view of another X-ray detector module according to the ninth embodiment.

As shown in FIG. 26B, the DAS chip 3289 may be placed outside the X-ray irradiation area, i.e., on a peripheral portion of the multilayer wiring board 3287, instead of giving an X-ray shield function to at least one of the plurality of thin printed wiring boards constituting the multilayer wiring board 3287. A lead shield plate 3271 is placed above the DAS chip 3289. The lead plate 3271 is mounted on a support 3270 for fixing the detector module 3280 in the shield housing.

Figure 26C:
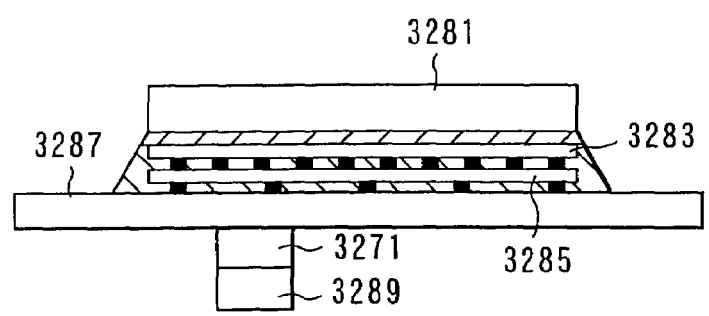
FIG. 26C is a sectional view of still another X-ray detector module according to the ninth embodiment.

The shield plate 3271 may be placed between the multilayer wiring board 3287 and the DAS chip 3289, as shown in FIG. 26C. In this case, the multilayer wiring board 3287 is electrically connected to the DAS chip 3289 by wire bonding instead of flip chip bonding.

Figure 26D:
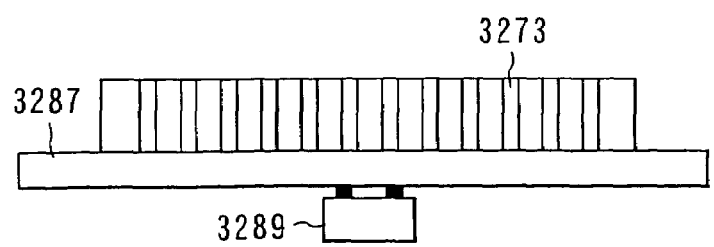
FIG. 26D is a sectional view of still another X-ray detector module according to the ninth embodiment.

If separators 3273 made of lead, molybdenum, or the like are inserted between the adjacent scintillator elements, as shown in FIG. 26D, since X-rays hardly pass through the scintillator 3281, the DAS chip 3289 may be placed inside the X-ray irradiation area.

According to this arrangement, incidence of X-rays on the DAS chip 3289 can be prevented, and hence the adverse effect of X-rays on a component having poor X-ray resistance characteristics can be prevented. If lead members are inserted between the multilayer wiring board 3287 and the DAS chip 3289 or a non-X-ray transmission type separator is used, in particular, as shown in FIGS. 26C and 26D, since no limitation is imposed on the position of the DAS chip 3289, a radiation detector can be easily manufactured.

In manufacturing the detector module 3280, the DAS chip 3289 and switching chip 3285 are connected to the multilayer wiring board 3287 by solder reflowing at 250° C. In the subsequent step, the photodiode chip 3283 is connected onto the switching chip 3285 at a relatively low temperature of 120° C. to 150° C. This procedure can prevent the surface of the photodiode chip 3283 from being exposed to a solder atmosphere and contaminated.

In the above connection steps, operating heat generated by the switching chip 3285 and DAS chip 3289 may be used. This head value is about 100 to 200 W in the overall radiation detector 3028, and the amount of heat required for the connection can be sufficiently ensured. There is no need to use a heater as in the prior art, and hence no large equipment is required for connection.

ON/OFF control on the transistors of the switching chip 3285 for changing the slice thickness will be described next.

Figure 28:
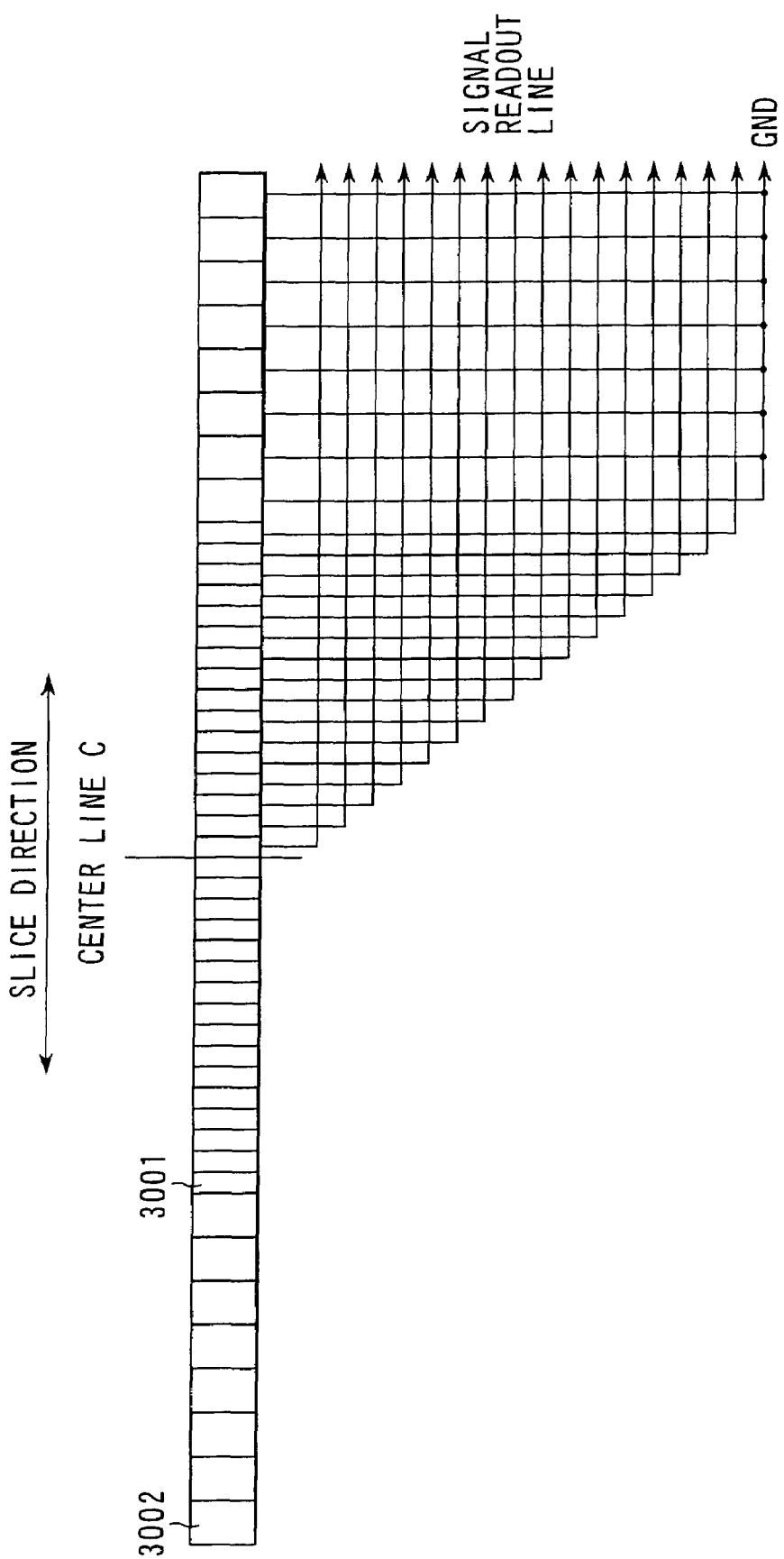
FIG. 28 is a view showing signal readout control corresponding to a condition of slice thickness of 0.5 mm×32 slices in the ninth embodiment.

As shown in FIG. 28, to obtain 32 0.5-mm thick slices, 32 transistors connected to the 32 0.5-mm wide photodiodes 3001 arrayed in the central portion are serially turned on. With this operation, the electrical signals detected by the 32 photodiodes 3001 are individually supplied to the DAS chips 3289. The charge generated by the remaining photodiodes 3002 leaks to the ground.

Figure 29:
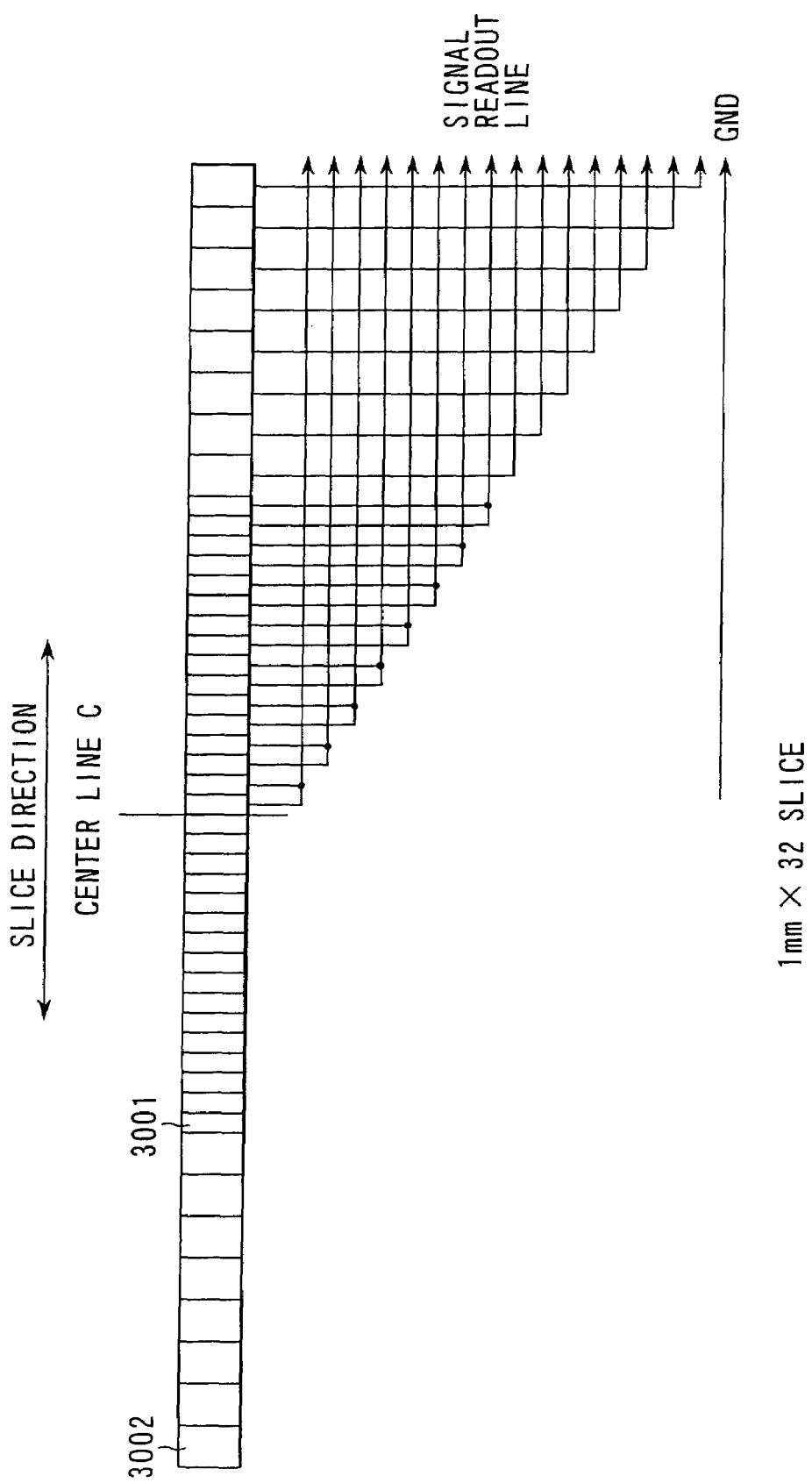
FIG. 29 is a view showing signal readout control corresponding to a condition of slice thickness of 1 mm×32 slices in the ninth embodiment.

As shown in FIG. 29, to obtain 32 1-mm thick slices, two transistors corresponding to each pair of adjacent photodiodes 3001 are simultaneously turned on. That is, the 16 transistors connected to the 1-mm wide photodiodes 3002 and the 16 pairs of transistors connected to the pairs of photodiodes 3001 are serially turned on.

Figure 30A:
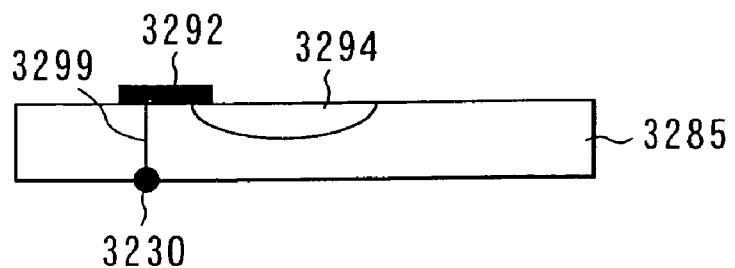
FIG. 30A is a schematic sectional view of a switching chip according to the ninth embodiment.

As shown in FIG. 30A, a photodiode 3294 formed in the upper surface of a silicon substrate 3285 of the photodiode chip 3283 is connected to an Al inter-connection 3292 formed on the surface of the silicon substrate 3285. This Al interconnection 3292 is extracted to the lower surface through a via interconnection 3299 extending through the silicon substrate 3285, and a bump 3230 is formed on the distal end of the Al interconnection 3292. With the use of the via interconnection 3299, an interconnection can be extracted to the lower surface of the photodiode chip 3283.

Figure 30B:
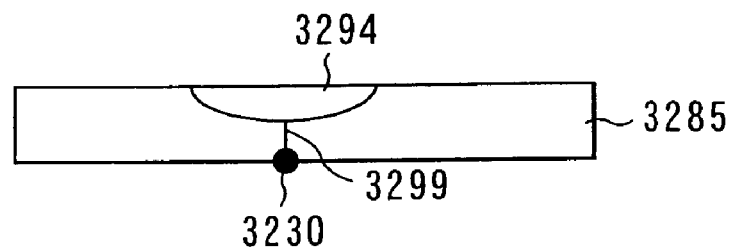
FIG. 30B is a schematic sectional view of another switching chip according to the ninth embodiment.
Figure 30C:
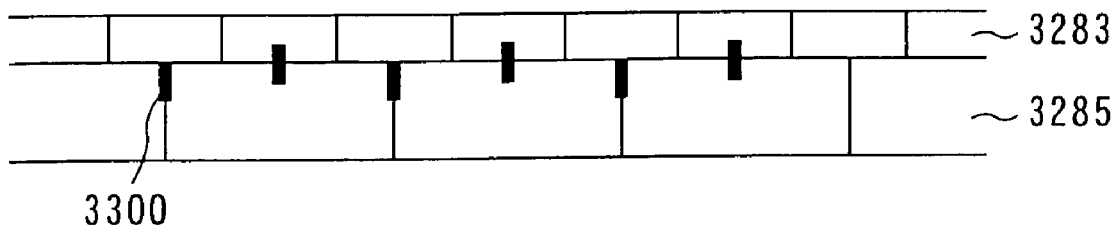
FIG. 30C is a schematic sectional view of still another switching chip according to the ninth embodiment.

As shown in FIG. 30B, the via interconnection 3299 may be formed immediately below the photodiode 3294. Alternatively, as shown in FIG. 30C, the photodiode chip 3283 and switching chip 3285 may be microbump-connected through a buried interconnection.

Note that the photodiode chip 3283 and switching chip 3285 may be connected through a multilayer wiring board.

The function of the detector module 3280 having the above arrangement will be described next.

In the prior art, since a detector and data acquisition system are discrete components, an output signal from each photodiode is transmitted as an analog signal to a data acquisition system 3085 through a flexible PC board. This structure requires a long flexible PC board. Consequently, the structure is susceptible to vibrations produced by rotation in scanning operation. As a result, for example, a connector is pulled by the flexible PC board and disconnected, and large noise is produced. Addition of detection elements leads to addition of flexible PC boards, resulting in more noise.

In contrast to this, the detector module 3280 is formed by commonly mounting the scintillator 3281, photodiode chip 3283, switching chip 3285, and DAS chip 3289 on the rigid multilayer wiring board 3287. Therefore, there is no need to extract signals through connectors and long flexible PC boards.

The signal extracted from the detector module 3280 and sent out to the system unit 3014 is a digital signal. For this reason, there is no chance of the occurrence of noise due to vibrations produced by rotation in scanning operation or the antenna effect of a flexible PC board, disconnection of a connector, and the like. This makes it possible to prevent generation of noise and the like and improve the image quality.

As the number of elements increases, the number of signal readout lines from a detector increases. If signals are extracted through connectors and flexible PC boards used in the conventional detector, the apparatus increases in size. In addition, the switch chip used for the conventional detector is placed in the same plane as that of each photodiode. As a consequence, the density of signals input to the switch chip increases, and the active area of each photodiode narrows. As a result, the sensitivity with respect to X-rays passing through the object decreases, and the obtained image becomes noisy. The generation of this noise becomes more conspicuous as the number of detection elements increases.

In contrast to this, the detector module 3280 is integrally formed by stacking the scintillator 3281, photodiode chip 3283, switching chip 3285, multilayer wiring board 3287, and DAS chip 3289. This structure offers space savings. In addition, the photodiodes of the photodiode chip 3283 are electrically connected to the transistors of the switching chip 3285 by bump connection. This multilayer structure realizes a space-saving electrical interconnection structure. Furthermore, the arrangement having this multilayer structure and bump connection structure can decrease the signal density as compared with the conventional detector in which many signal interconnections are connected to transistors arranged in the same plane as that of photodiodes. This makes it possible to ensure a wide active area for each photodiode.

According to the above arrangement, the following effects can be obtained.

(1) Imaging can be performed in a wide range in unit time with high resolution without increasing the apparatus size. In addition, the sensitivity to X-rays can be improved, and hence the quality of a resultant image can be improved.

(2) Unlike the conventional detector, there is no need to use a flexible PC board and backplane substrate. This makes it possible to reduce the outer dimensions of the detector unit. In addition, no DAS chassis is required, and hence space saving can be made in the CT apparatus.

(3) The protrusion of the front cover as in the conventional detector can be eliminated. Therefore, the dome opening seems to be wider than that in the prior art, thus reducing the oppressive feeling of a patient. In addition, this improves the accessibility of an operator or doctor to a patient.

(3) There is no interference between the gantry and the bed, and a large tilt angle can be ensured. Therefore, a patient in a conformable position can be imaged.

(4) If the detector system according to the present invention is applied to a conventional apparatus, a tomographic image with a slice thickness larger than in the prior art can be obtained.

(5) The accessibility with respect to units mounted deep inside the detection unit can be improved.

(6) The weight of the detector unit can be reduced. As a consequence, when the detector unit is rotated in imaging operation, the influences of gantry shake due to the rotation can be reduced as compared with the prior art.

(7) The number of components used is smaller than that of the conventional detector, and hence a reduction in cost an be achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiation detecting system comprising:
  a scintillator for converting an X-ray incident from a surface side into light;

at least one photodiode chip having a plurality of photodiodes for converting the converted light into electrical signals;

at least one switching chip having a plurality of switching elements for reading out a plurality of signals from said plurality of photodiodes;

at least one data acquisition chip having a plurality of data acquisition systems for amplifying the plurality of readout signals and converting the signals into digital signals; and a rigid printed wiring board on which said photodiode chip, said switching chip, and said data acquisition chip are commonly mounted.

2. A detecting system according to claim 1, wherein said photodiode chip is bump-connected to said rigid printed wiring board through a plurality of via interconnections which are connected to said plurality of photodiodes and extend through a semiconductor substrate from an upper surface to a lower surface, said switching chip is connected to said rigid printed wiring board by flip chip bonding, and said data acquisition chip is connected to said rigid printed wiring board by flip chip bonding.

3. A radiation detecting system comprising:

a scintillator for converting an X-ray incident from a surface side into light;

at least one photodiode chip having a plurality of photodiodes for converting the converted light into electrical signals;

at least one switching chip having a plurality of switching elements for reading out a plurality of signals from said plurality of photodiodes;

at least one data acquisition chip having a plurality of data acquisition systems for amplifying the plurality of readout signals and converting the signals into digital signals; and a rigid multilayer wiring board on which said photodiode chip, said switching chip, and said data acquisition chip are commonly mounted.

4. A detecting system according to claim 3, wherein said photodiode chip is bump-connected to an upper surface of said multilayer wiring board through a plurality of via interconnections which are connected to said plurality of photodiodes and extend through a semiconductor substrate from an upper surface to a lower surface, said switching chip is connected to the upper surface of said rigid multilayer wiring board by flip chip bonding, and said data acquisition chip is connected to a lower surface of said rigid multilayer wiring board by flip chip bonding.

5. A detecting system according to claim 3, wherein said photodiode chip is bump-connected to an upper surface of said multilayer wiring board through a plurality of via interconnections which are connected to said plurality of photodiodes and extend through a semiconductor substrate from an upper surface to a lower surface, said switching chip is connected to a lower surface of said rigid multilayer wiring board by flip chip bonding, and said data acquisition chip is connected to the lower surface of said rigid multilayer wiring board by flip chip bonding.

6. A detecting system according to claim 3, wherein a rear surface of said switching chip is bonded to the upper surface of said multilayer wiring board, a rear surface of said photodiode chip is bonded to an upper surface of said switching chip, and said data acquisition chip is bonded to the lower surface of said multilayer wiring board.

7. A detecting system according to claim 6, wherein the plurality of photodiodes are connected to the plurality of switching elements through a plurality of first via interconnections extending through the photodiode substrate from an upper surface to a lower surface, the plurality of switching elements are connected to a plurality of upper surface interconnections on said multilayer wiring board through a plurality of second via interconnections extending through a switching element board from an upper surface to a lower surface, and said data acquisition chip is connected a plurality of lower surface interconnections of said multilayer wiring board by flip chip bonding.

8. A detecting system according to claim 6, wherein said data acquisition chip is placed on a peripheral portion of said multilayer wiring board.

9. A detecting system according to claim 8, further comprising a plurality of X-ray shield plates placed above said data acquisition chip.

10. A radiation detecting system comprising:

a scintillator for converting an X-ray incident from a surface side into light;

at least one photodiode chip having a plurality of photodiodes for converting the converted light into electrical signals;

at least one switching chip having a plurality of switching elements for reading out a plurality of signals from said plurality of photodiodes;

at least one data acquisition chip having a plurality of data acquisition systems for amplifying the plurality of readout signals and converting the signals into digital signals;

a first rigid printed wiring board on which said photodiode chip and said switching chip are mounted;

a second rigid printed wiring board on which said data acquisition chip is mounted; and a connector for detachably connecting said first rigid printed wiring board to said second rigid printed wiring board.

11. A system according to claim 10, wherein said photodiode chip is bump-connected to upper surface interconnections of said first rigid printed wiring board through a plurality of via interconnections which are connected to said plurality of photodiodes and extend through a semiconductor substrate from an upper surface to a lower surface.

12. A radiation detection system comprising:

a detection element group constituted by a plurality of detection elements for detecting X-rays;

data acquisition means for acquiring output data from said detection element group;

a substrate on which at least one of said detection element group and said data acquisition means is mounted; and means for forming said detection element group, said data acquisition means, and said substrate into a multilayer structure.

13. A radiation detection system comprising:

a scintillator block for converting X-nays into light;

a photodiode array for converting the light into electrical signals;

a switch for selecting a photodiode, from said photodiode array, from which an electrical signal is to be output;

a data acquisition chip for acquiring data output from said photodiode array selected by said switch; and means for integrating said scintillator block, said photodiode array, said switch, and said data acquisition chip.

14. A radiation detection system comprising:
a detection element group constituted by a plurality of detection elements for detecting X-rays;
a first substrate on which said detection element group is mounted;
a data acquisition chip for acquiring output data from said detection element group;
a second substrate on which said data acquisition chip is mounted; and
connection means for connecting said first and second substrates in a one-to-one correspondence.

15. A system according to claim 14, wherein said connection means comprises a connector for electrically connecting said first and second substrates.

16. A system according to claim 15, wherein
said first substrate has said detection element group mounted on an X-ray incident surface side,
said second substrate has said data acquisition chip mounted on the other surface side with respect to the X-ray incident surface, and
said connection means connects through the connector a surface of said first substrate on which said detection element group is not mounted to a surface of said second substrate on which said data acquisition chip is not mounted.

17. A system according to claim 14, wherein said second substrate has said data acquisition chip mounted in an X-ray transmission area, and has the connector mounted outside the X-ray transmission area.

18. An X-ray CT apparatus comprising:
an X-ray source which emits X-rays while rotating around an object to be examined;
a radiation detection system having a plurality of detection elements for detecting X-rays passing though the object, which are arranged in row and column directions; and
reconstruction means for reconstructing a CT image of the object on the basis of the projection data,
wherein said radiation detection system includes
a scintillator for convening an X-ray incident from a surface side into light,
at least one photodiode chip having a plurality of photodiodes for converting the converted light into electrical signals,
at least one switching chip having a plurality of switching elements for reading out a plurality of signals from said plurality of photodiodes,
at least one data acquisition chip having a plurality of data acquisition systems for amplifying the plurality of readout signals and converting the signals into digital signals, and
a rigid printed wiring board on which said photodiode chip, said switching chip, and said data acquisition chip are commonly mounted.

19. An X-ray CT apparatus comprising:
an X-ray source which emits X-rays while rotating around an object to be examined;
a radiation detection system having a plurality of detection elements for detecting X-rays passing through the object, which are arranged in row and column directions; and
reconstruction means for reconstructing a CT image of the object on the basis of the projection data, wherein said radiation detection system includes a scintillator for converting an X-ray incident from a surface side into light,
at least one photodiode chip having a plurality of photodiodes for converting the converted light into electrical signals,
at least one switching chip having a plurality of switching elements for reading out a plurality of signals from said plurality of photodiodes,
at least one data acquisition chip having a plurality of data acquisition systems for amplifying the plurality of readout signals and converting the signals into digital signals, and
a rigid multilayer printed wiring board on which said photodiode chip, said switching chip, and said data acquisition chip are commonly mounted.

20. An X-ray CT apparatus comprising:
an X-ray source which emits X-rays while rotating around an object to be examined;
a radiation detection system having a plurality of detection elements for detecting X-rays passing through the object, which are arranged in row and column directions; and
reconstruction means for reconstructing a CT image of the object on the basis of the projection data,
wherein said radiation detection system includes
a scintillator for converting an X-ray incident from a surface side into light,
at least one photodiode chip having a plurality of photodiodes for converting the converted light into electrical signals,
at least one switching chip having a plurality of switching elements for reading out a plurality of signals from said plurality of photodiodes,
at least one data acquisition chip having a plurality of data acquisition systems for amplifying the plurality of readout signals and converting the signals into digital signals,
a first rigid printed wiring board on which said photodiode chip and said switching chip are mounted;
a second rigid printed wiring board on which said data acquisition chip is mounted, and
a connector for detachably connecting said first rigid printed wiring board to said second rigid printed wiring board.

21. An X-ray CT apparatus comprising:
an X-ray source which emits X-rays while rotating around an object to be examined;
a radiation detector having a plurality of detection elements for detecting X-rays passing through the object, which are arranged in row and column directions;
data acquisition means for acquiring projection data associated with the object by using an output from said radiation detector;
switch means for selecting data from the plurality of detection elements which are to be output to said data acquisition means;
reconstruction means for reconstructing a CT image of the object on the basis of the projection data; and
means for forming said radiation detector and at least one of said data acquisition means and said switch into a multilayer structure.

22. An X-ray CT apparatus comprising:

an X-ray source which emits X-rays while rotating around an object to be examined;

a radiation detector having a plurality of detection elements for detecting X-rays passing through the object, which are arranged in row and column directions;

data acquisition means for acquiring projection data associated with the object by using an output from said radiation detector;

reconstruction means for reconstructing a CT image of the object on the basis of the projection data; and connection means for connecting in a one-one-one correspondence a first substrate on which said X-ray detector is mounted to a second substrate on which said data acquisition means is mounted.

* * * * *